United States Patent [19]
Nudelman et al.

[11] Patent Number: 6,130,248
[45] Date of Patent: Oct. 10, 2000

[54] TRICARBOXYLIC ACID-CONTAINING OXYALKYL ESTERS AND USES THEREOF

[75] Inventors: Abraham Nudelman, Rehovot, Israel; Ada Rephaeli, North Caldwell, N.J.

[73] Assignees: Bar-ILAn University, Ramat-Gan; Mor Research Applications, Ltd., Givat Shmuel, both of Israel; Beacon Laboratories, Inc., Phoenix, Md.

[21] Appl. No.: 08/781,905

[22] Filed: Dec. 30, 1996

[51] Int. Cl.[7] .................. A61K 31/225; C07C 69/612; C07C 69/67

[52] U.S. Cl. .................. 514/547; 514/3; 514/12; 514/34; 514/49; 514/245; 514/615; 514/648; 560/155; 560/179; 560/187; 560/199

[58] Field of Search .................. 560/155, 179, 560/187, 199; 514/547

[56] References Cited

U.S. PATENT DOCUMENTS

| | | | |
|---|---|---|---|
| 2,940,855 | 6/1960 | Beavers et al. | 96/107 |
| 3,219,630 | 11/1965 | Sidi | 260/67 |
| 3,293,220 | 12/1966 | Minami et al. | 260/67 |
| 3,336,262 | 8/1967 | Sidi | 260/67 |
| 3,720,706 | 3/1973 | Lapporte et al. | 260/494 |
| 3,812,176 | 5/1974 | Lapporte et al. | 260/494 |
| 3,931,412 | 1/1976 | Kensler, Jr. et al. | 424/313 |
| 4,012,526 | 3/1977 | Kensler, Jr. et al. | 424/313 |
| 4,105,681 | 8/1978 | Bollag et al. | 260/404 |
| 4,123,552 | 10/1978 | Kensler, Jr. et al. | 424/311 |
| 4,198,416 | 4/1980 | Koeda et al. | 424/266 |
| 4,215,215 | 7/1980 | Bollag et al. | 542/427 |
| 4,541,944 | 9/1985 | Sanderson | 252/95 |
| 4,545,784 | 10/1985 | Sanderson | 8/107 |
| 4,613,505 | 9/1986 | Mizushima et al. | 424/80 |
| 4,699,925 | 10/1987 | Uchida et al. | 514/559 |
| 4,760,057 | 7/1988 | Alexander | 514/187 |
| 4,885,311 | 12/1989 | Parish et al. | 514/549 |
| 4,900,478 | 2/1990 | Gross | 260/408 |
| 4,916,230 | 4/1990 | Alexander | 546/318 |
| 5,025,029 | 6/1991 | Perrine | 514/381 |
| 5,158,773 | 10/1992 | Gross | 424/401 |
| 5,185,436 | 2/1993 | Villa et al. | 536/4.1 |
| 5,196,567 | 3/1993 | Uchida et al. | 560/102 |
| 5,200,553 | 4/1993 | Nudelman et al. | 560/263 |
| 5,216,004 | 6/1993 | Perrine | 514/381 |
| 5,569,675 | 10/1996 | Rephaeli et al. | 514/547 |
| 5,710,176 | 1/1998 | Rephaeli et al. | 514/548 |

FOREIGN PATENT DOCUMENTS

| | | |
|---|---|---|
| 0 056 189 A1 | 7/1982 | European Pat. Off. . |
| 0 319 316 A2 | 6/1989 | European Pat. Off. . |
| 0 371 789 A2 | 6/1990 | European Pat. Off. . |
| 1386096 | 12/1965 | France . |
| 1540418 | 9/1968 | France . |
| 58-15912 | 1/1983 | Japan . |
| 63-101348 | 5/1988 | Japan . |
| 1177442 | 1/1970 | United Kingdom . |
| 1 220 447 | 1/1971 | United Kingdom . |
| 1 382 010 | 1/1975 | United Kingdom . |
| 2126082 | 3/1984 | United Kingdom . |
| WO92/14706 | 9/1992 | WIPO . |
| WO93/19778 | 10/1993 | WIPO . |
| WO94/01415 | 1/1994 | WIPO . |

OTHER PUBLICATIONS

Brant and Conklin, "Acrolein Diacylates", Chem. Abstracts, vol. 40, p. 3127, 1946.

Carstea, et al., "Analogues of Butyric Acid that increase the Expression of Transfected DNAs", Biochem. Biophys. Res. Com., vol. 192, No. 2, pp. 649–656, 1993.

Cheng, et al., "Functional Activation of the Cystic Fibrosis Trafficking Mutant deltaF508–CFTR by Overexpression", American Journal of Physiology, vol. 268, No. 4, pp. L615–L624, 1995.

Ingram and Thomas, "The Electron Impact Induced Fragmentation of Geminal Dialkanoates", Organic Mass Spectrometry, vol. 12, No. 4, pp. 216–221, 1977.

Kamiya, et al., "Pharmaceutical Patches Comprising Water–Soluble Adhesive Sheet", Chem. Abstracts, vol. 126, Abstract 162263, 1997.

Man, et al., "Boron Fluoride Catalyzed Addition of Aliphatic Anhydrides to Aldehydes", J. Am. Chem. Soc., pp. 847–848, 1950.

Miller, et al., "Clinical Pharmacology of Sodium Butyrate in Patients with Acute Leukemia", Eur. J. Cancer Clin Oncol. vol. 23, No. 9, pp. 1283–1287, 1987.

Mosher and Kehr, "The Oxidation of Aliphatic Esters with Lead Tetraacetate", J. Am. Chem. Soc., vol. 82, pp. 5342–5345, 1960.

Nielsen and Bundgaard, "Evaluation of Glycolamide Esters and Various Other Esters of Aspirin as True Aspirin Prodrugs", J. Medicinal Chem., vol. 35, pp. 687–694, 1992.

Novogrodsky, et al., "Effect of Polar Organic Compounds on Leukemic Cells", Cancer, vol. 51, No. 1, pp. 9–14, 1983.

Nudelman, et al., "Novel Anticancer Prodrugs of Butyric Acid", J. Med. Chem., vol. 35, pp. 687–694, 1992.

Oh, et al., "Convenient Synthesis of Geminal Biscarboxylates: Searching for an Efficient Route to HR 916B", Korean J. Med. Chem., vol. 6, No. 2, pp. 259–262, 1996.

Rephaeli, et al., "Butyrate–Induced Differentiation in Leukemic Myeloid Cells: in vitro and in vivo Studies", International Journal of Oncology, vol. 4, No. 6, pp. 1387–1391, 1994.

(List continued on next page.)

*Primary Examiner*—Richard L. Raymond
*Attorney, Agent, or Firm*—Kenyon & Kenyon

[57] ABSTRACT

This invention relates to compositions for and methods of treating, preventing or ameliorating cancer and other proliferative diseases as well as methods of inducing wound healing, treating cutaneous ulcers, treating gastrointestinal disorders, treating blood disorders such as anemias, immunomodulation, enhancing recombinant gene expression, treating insulin-dependent patients, treating cystic fibrosis patients, inhibiting telomerase activity, treating virus-associated tumors, especially EBV-associated tumors, augmenting expression of a tumor suppressor gene and inducing tolerance to an antigen. The methods of the invention use tricarboxylic acid substituted oxyalkyl esters.

12 Claims, 9 Drawing Sheets

OTHER PUBLICATIONS

Sanderson, et al., "Bleach Compositions", Chem. Abstracts, vol. 102, Abstract 47772, 1985.

Sher, et al., "Extended Therapy with Intravenous Arginine Butyrate in Patients with Beta—Hemoglobinopathies", New England Journal of Medicine, vol. 332, No. 24, pp. 1606–1610, 1995.

Scheeren and Tax, "Mixed Acylals; Synthesis of Alkylidene Carboxylate Formates", Synthesis, vol. 3, pp. 151–153, 1973.

Smith, et al., "Incorporation of Tributyrin Enhances the Expression of a Reporter Gene in Primary and Immortalized Cell Lines", Biotechniques, vol. 18, No. 5, pp. 852–855, 1995.

Stamatoyannopoulos, et al., "Therapeutic Approaches to Hemoglobin Switching in Treatment of Hemoglobinopathies", Ann. Rev. Med., vol. 43, pp. 497–522, 1992.

Tang, et al., "Butyrate–Inducible and Tumor–Restricted Gene Expression by Adenovirus Vectors", Cancer Gene Therapy, vol. 1, No. 1, pp. 15–20, 1994.

Toyobo Co., "Electroconductive Resin Compositions", Chem. Abstracts, vol. 103, Abstract 125229, 1985.

Tomiska and Spousta, "Low–Molecular Polyoxymethylene Diacetates from Trioxane", Angew. Chem. Internat. Edit., vol. 1, No. 4, p. 211, 1962.

Nielson and Bundgaard, "Evaluation of Glycolamide Esters and Various Other Esters of Aspirin as True Aspirin Prodrugs", J. Medicinal Chem. vol. 32, pp. 727–734, 1989.

Kamiya et al., Chemical Abstracts, vol. 126, abstract 162263, 1997.

Oh et al., Chemical Abstracts, vol. 126, abstract 131271, 1997.

Toyobo Co., Chemical Abstracts, vol. 103, abstract 125229, 1985.

Sanderson et al., Chemical Abstract, vol. 102, abstract 47772, 1985.

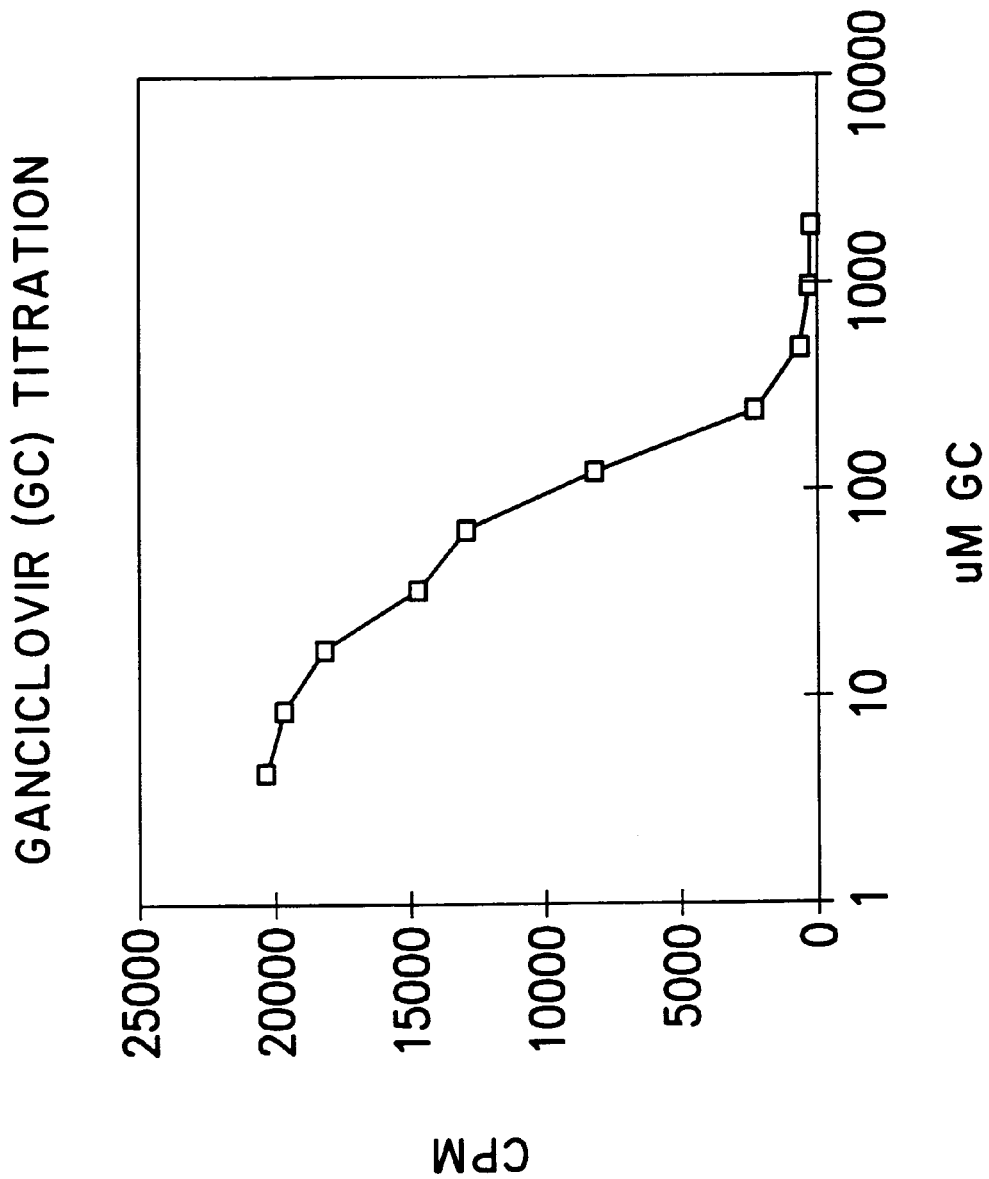

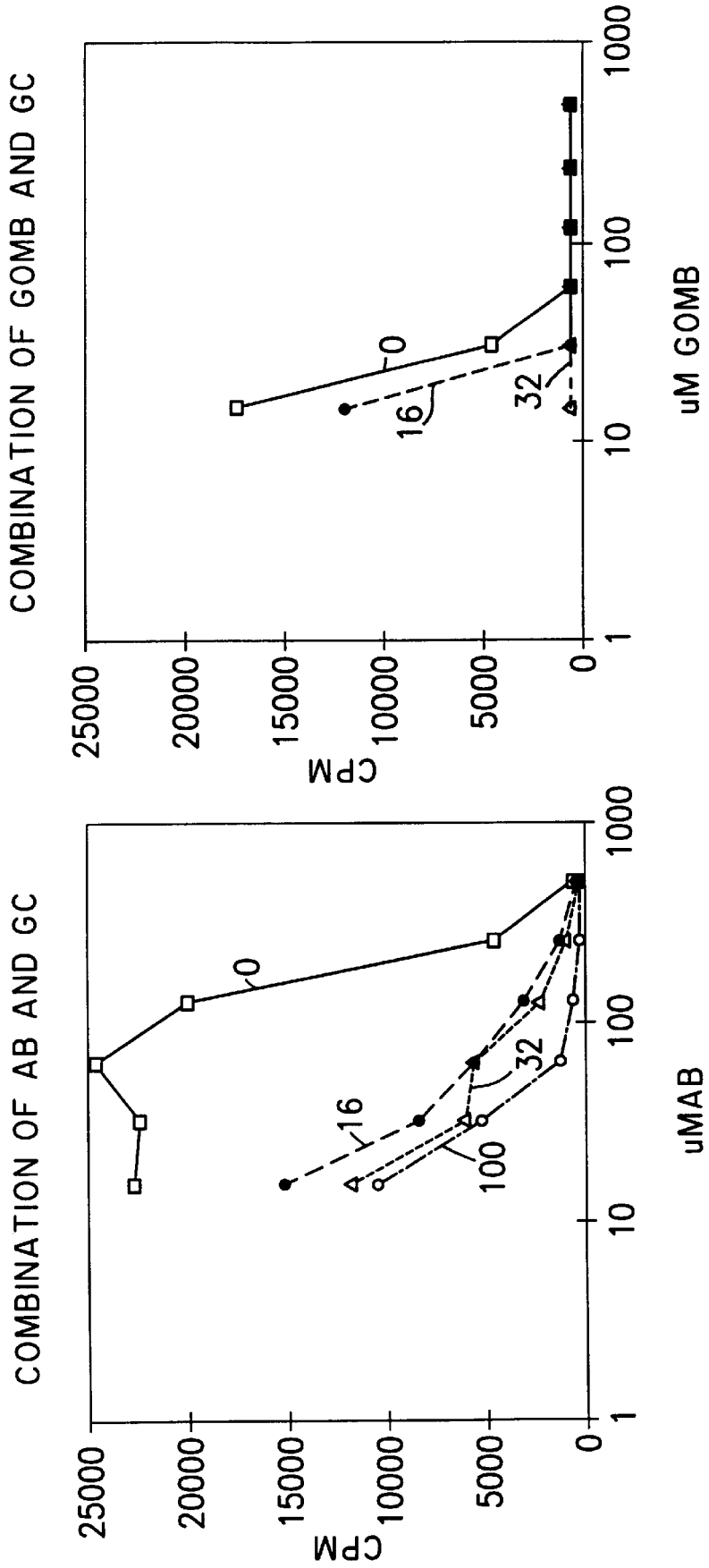

TRICARBOXYLIC ACID-CONTAINING OXYALKYL ESTERS AND USES THEREOF

FIELD OF THE INVENTION

This invention relates to compositions for and methods of treating, preventing or ameliorating cancer and other proliferative diseases as well as methods of inducing wound healing, treating cutaneous ulcers, treating gastrointestinal disorders, treating blood disorders such as anemias, immunomodulation, enhancing recombinant gene expression, treating insulin-dependent patients, treating cystic fibrosis patients, inhibiting telomerase activity, treating virus-associated tumors, especially EBV-associated tumors, augmenting expression of tumor suppressor genes and inducing tolerance to antigens. The methods of the invention use tricarboxylic acid substituted oxyalkyl esters.

BACKGROUND OF THE INVENTION

Butyric acid (BA) is a natural product. It is supplied to mammals from two main sources: 1) the diet, mainly from dairy fat, and 2) from the bacterial fermentation of unabsorbed carbohydrates in the colon, where it reaches mM concentrations (Cummings, *Gut* 22:763–779, 1982; Leder et al., *Cell* 5:319–322, 1975).

BA has been known for nearly the last three decades to be a potent differentiating and antiproliferative agent in a wide spectra of neoplastic cells in vitro (Prasad, *Life Sci.* 27:1351–1358, 1980). In cancer cells, BA has been reported to induce cellular and biochemical changes, e.g., in cell morphology, enzyme activity, receptor expression and cell-surface antigens (Nordenberg et al., *Exp. Cell Res.* 162:77–85, 1986; Nordenberg et al., *Br. J. Cancer* 56:493–497, 1987; and Fishman et al., *J. Biol. Chem.* 254:4342–4344, 1979).

Although BA or its sodium salt (sodium butyrate, SB) has been the subject of numerous studies, its mode of action is unclear. The most specific effect of butyric acid is inhibition of nuclear deacetylase(s), resulting in hyperacetylation of histones H3 and H4 (Riggs, et al., *Nature* 263:462–464, 1977). Increased histone acetylation following treatment with BA has been correlated with changes in transcriptional activity and the differentiated state of cells (Thorne et al., *Eur. J. Biochem.* 193:701–713, 1990). BA also exerts other nuclear actions, including modifications in the extent of phosphorylation (Boffa et al., *J. Biol. Chem.* 256:9612–9621, 1981) and methylation (Haan et al., *Cancer Res.* 46:713–716, 1986). Other cellular organelles, e.g., cytoskeleton and membrane composition and function, have been shown to be affected by BA (Bourgeade et al., *J. Interferon Res.* 1:323–332, 1981). Modulations in the expression of oncogenes and suppressor genes by BA were demonstrated in several cell types. Toscani et al., reported alterations in c-myc, p53 thymidine kinase, c-fos and AP2 in 3T3 fibroblasts (*Oncogene Res.* 3:223–238, 1988). A decrease in the expression of c-myc and H-ras oncogenes in B16 melanoma and in c-myc in HL-60 promyelocytic leukemia was also reported (Prasad et al., *Biochem. Cell Biol.* 68:1250–1255, 1992; and Rabizadeh et al., *FEBS Lett.* 328:225–229, 1993).

BA has been reported to induce apoptosis, i.e., programmed cell death. SB has been shown to produce apoptosis in vitro in human colon carcinoma, leukemia and retinoblastoma cell lines (Bhatia et al., *Cell Growth Diff.* 6:937–944, 1995; Conway et al., *Oncol. Res.* 7:289–297, 1993; Hague et al.; *Int. J. Cancer* 60:400–406, 1995). Apoptosis is the physiological mechanism for the elimination of cells in a controlled and timely manner. Organisms maintain a delicate balance between cell proliferation and cell death, which when disrupted can tip the balance between cancer, in the case of over accumulation of cells, and degenerative diseases, in the case of premature cell losses. Hence, inhibition of apoptosis can contribute to tumor growth and promote progression of neoplastic conditions.

The promising in vitro antitumor effects of BA and BA salts led to the initiation of clinical trials for the treatment of cancer patients with observed minimal or transient efficacy. [Novogrodsky et al., *Cancer* 51:9–14, 1983; Rephaeli et al., *Intl. J. Oncol.* 4:1387–1391, 1994; Miller et al., *Eur. J. Cancer Clin. Oncol.* 23:1283–1287, 1987].

Clinical trials have been conducted for the treatment of β-globin disorders (e.g., β-thalassemia and sickle-cell anemia) using BA salts. The BA salts elevated expression of fetal hemoglobin (HbF), normally repressed in adults, and favorably modified the disease symptoms in these patients (Stamatoyannopouos et al., *Ann. Rev. Med.* 43:497–521, 1992). In this regard, arginine butyrate (AB) has been used in clinical trials with moderate efficacy (Perrine et al., *N. Eng. J. Med.* 328:81–86, 1993; Sher et al., *N. Eng. J. Med.* 332:1606–1610, 1995). The reported side effects of AB included hypokalemia, headache, nausea and vomiting in β-thalassemia and sickle-cell anemia patients.

Butyric acid derivatives with antitumor activity and immunomodulatory properties have been reported in U.S. Pat. No. 5,200,553 and by Nudelman et al., 1992, *J. Med. Chem.* 35:687–694. The most active butyric acid prodrug reported in these references was pivaloyloxymethyl butyrate (AN-9). None of the compounds disclosed in these references included carboxylic acid-containing oxyalkyl compounds of this invention.

BA and/or its analogues have also been reported to increase the expression of transfected DNA (Carstea et al., 1993, *Biophys. Biohem. Res. Comm.* 192:649; Cheng et al., 1995, *Am. J. Physical* 268:L615–L624) and to induce tumor-restricted gene expression by adenovirus vectors (Tang et al., 1994, *Cancer Gene Therapy* 1:15–20). Tributyrin has been reported to enhance the expression of a reporter gene in primary and immortalized cell lines (Smith et al., 1995, *Biotechniques* 18:852–835).

However, BA and its salts are normally metabolized rapidly and have very short half-lives in vivo, thus the achievement and maintenance of effective plasma concentrations are problems associated with BA and BA salts, particularly for in vivo uses. BA and BA salts have required large doses to achieve even minimal therapeutic effects. Because of the high dosage, fluid overload and mild alkalosis may occur. Patients receiving BA emanate an unpleasant odor that is socially unacceptable.

While BA salts have been shown to increase HbF expression, and appear to hold therapeutic promise with low toxicity in cancer patients, they nevertheless have shown low potency in in vitro assays and clinical trials. There also remains a need to identify compounds as effective or more effective than BA or BA salts as differentiating or antiproliferating agents for the treatment of cancers. Such compounds need to have higher potency than BA without the problems associated with BA (such as bad odor). Consequently, there remains a need for therapeutic compounds that either deliver BA to cells in a longer acting form or which have similar activity as BA but a longer duration of effectiveness in vivo.

The compounds of this invention address these needs and are more potent than BA or BA salts for treating cancers and other proliferative diseases, for treating gastrointestinal disorders, for wound healing and for treating blood disorders such as thalassemia, sickle cell anemia and other anemias, for modulating an immune response, for enhancing recombinant gene expression, for treating insulin-dependent patients, for treating cystic fibrosis patients, for inhibiting telomerase activity, for detecting cancerous or malignant cells, for treating virus-associated tumors, especially EBV-associated tumors, for augmenting expression of a tumor suppressor gene and for inducing tolerance to an antigen. For example, one of the advantages of the compounds of the invention is increased water solubility of the free carboxylic acids compounds of the invention and their salts, and easier administration, especially for intravenous administration.

SUMMARY OF THE INVENTION

Accordingly, one embodiment of the present invention is directed to a method of treating preventing or ameliorating cancer and other proliferative disorders using compounds represented by Formula (I):

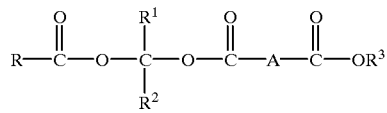

wherein
R is benzyl, 2-pyridylmethyl, 3-pyridylmethyl, 4-pyridylmethyl, or $C_3$ to $C_{10}$ alkyl, alkenyl, or alkynyl, any of which can be optionally substituted with halo, trifluoromethyl, amino, hydroxy, alkoxy, carbonyl, aryl or heteroaryl;

$R^1$ and $R^2$ are independently H, lower alkyl or lower alkenyl;

A is aryl, heteroaryl, or $C_1$ to $C_8$ alkyl, alkenyl, or alkynyl, wherein alkyl, alkenyl and alkynyl are optionally substituted with one or more of hydroxy, halo, lower alkyl, alkoxy, carbonyl, thiol, lower alkylthio, aryl or heteroaryl;

$R^3$ is H, alkyl, alkenyl, aryl, aralkyl, heteroaryl, heteroaralkyl, or —$CR^1R^2$—O—C(O)—R; and pharmaceutically-acceptable salts thereof.

The above compounds can be used in all the methods of the invention. In a preferred embodiment, the compounds used in this and the other methods of the invention are those of Formula I, wherein R is n-propyl; benzyl; 3-(phenyl)propyl; 2-chloroethyl; 2-propenyl; 2-(3-pyridyl)ethyl, 2-, 3- or 4-pyridylmethyl; or 3-(2-, 3- or 4-pyridyl)propyl;

A is $C_2$ to $C_6$ alkyl with up to three methyl substituents;

$R^3$ is H or lower alkyl, or —$CR^1R^2$—O—C(O)—R; and pharmaceutically-acceptable salts thereof.

In a more preferred embodiment, the compounds used in this and the other methods of the invention are mono-(butyroyloxymethyl)glutarate (GOMB), bis-(butyroyloxymethyl)glutarate (bisGOMB), mono-(1-butyroyloxyethyl)glutarate, bis-(1-butyroyloxyethyl) glutarate, and most preferably, GOMB.

The methods of the present invention are particularly useful for treating, preventing or ameliorating the effects of cancer and other proliferative disorders by acting as antiproliferative or differentiating agents in subjects afflicted with such anomalies. Such disorders include but are not limited to leukemias, such as acute promyelocytic leukemia, acute myeloid leukemia, and acute myelomonocytic leukemia; other myelodysplastic syndromes, multiple myeloma such as but not limited to breast carcinomas, cervical cancers, melanomas, colon cancers, nasopharyngeal carcinoma, non-Hodgkins lymphoma (NHL), Kaposi's sarcoma, ovarian cancers, pancreatic cancers, hepatocarcinomas, prostate cancers, squamous carcinomas, other dermatologic malignancies, teratocarcinomas, T-cell lymphomas, lung tumors, gliomas, neuroblastomas, peripheral neuroectodermal tumors, rhabdomyosarcomas, and prostate tumors and other solid tumors. It is also possible that compounds of Formula (I) have anti-proliferative effects on non-cancerous cells as well, and may be of use to treat benign tumors and other proliferative disorders such as psoriasis. Preferred is the method for treating or ameliorating leukemia, squamous cell carcinoma and neuroblastoma.

Another embodiment of the present invention is directed to methods of treating, preventing or ameliorating cancer and other proliferative disorders by administering a therapeutically-effective amount of a compound of Formula (I) to a subject suffering from such disorders together with a pharmaceutical agent (e.g., a known antiproliferative, differentiating or oncostatic agents) to thereby enhance the action of these agents. Such agents include but are not limited to, cytokines, interleukins, anti-cancer agents, chemotherapeutic agents, antibodies, conjugated antibodies, immune stimulants, antibiotics, hormone antagonists, and growth stimulants. The compounds of the invention can be administered prior to, after or concurrently with any of the agents.

Yet another embodiment of the invention is directed to a method of ameliorating the effects of a cytotoxic agent which comprises adminstering a therapeutically-effective amount of an cytotoxic agent with a compound of Formula I to a mammalian patient for a time and in an amount to induce growth arrest of rapidly-proliferating epithelial cells of the patient and thereby protect those cells from the cytotoxic effects of the agent. The cytotoxic agent can be a chemotherapeutic agent, an anticancer agent, or radiation therapy. Rapidly proliferating rapidly-proliferating epithelial cells are found in hair follicles, the gastrointestinal tract, the bladder and the bone marrow, for example. Such cells include bone marrow stem cells, hair follicle cells, or intestinal cryt cells. In accordance with the invention the cytotoxic agent and the compound of Formula I can be administered simultanously, or the cytotoxic agent can be administered prior to or after the compound of the invention. Administration (simulataneously or separately) can be done systemically or topically as determined by the indication. In addition, when the cytotoxic agent is radiation therapy, the compounds of the invention can be administered to a cancer patient pre- or post-radiation therapy to treat or ameliorate the effects of cancer.

A still further embodiment of the invention is directed to a method of inducing wound healing, treating cutaneous ulcers or treating a gastrointestinal disorder by administering a therapeutically-effective amount of a compound of Formula (I) to a subject in need of such treatment. The cutaneous ulcers which can be treated in accordance with the methods of the invention include leg and decubitus ulcers, stasis ulcers, diabetic ulcers and atherosclerotic ulcers. With respect to wound healing, the compounds are useful in treating abrasions, incisions, burns, and other wounds. Gastrointestinal disorders treatable by the methods of the invention include colitis, inflammatory bowel disease, Crohn's disease and ulcerative colitis.

The invention is further directed to a method of treating blood disorders by administering a therapeutically-effective amount of a compound of Formula (I) to a patient. The blood disorders treatable in accordance with the invention include, but are not limited to, thalassemias, sickle cell anemias, infectious anemias, aplastic anemias, hypoplastic and hypoproliferative anemias, sideroblastic anemias, myelophthisic anemias, antibody-mediated anemias, anemias due to chronic diseases and enzyme-deficiencies, and anemias due to blood loss, radiation therapy and chemotherapy. In this regard, these methods can include increasing hemoglobin content in blood by administering a therapeutically-effective amount of a compound of Formula (I) to a subject.

Another embodiment of the invention is directed to a method of modulating an immune response in a host by administering an amount of a compound of Formula I effective to modulate said immune response. Modulation of the immune response includes enhancing cytokine secretion, inhibiting or delaying apoptosis in polymorphonuclear cells, enhancing polymorphonuclear cell function by augmenting hematopoietic growth factor secretion, inducing expression of cell surface antigens in tumor cells, and enhancing progenitor cell recovery after bone marrow transplantation.

A further embodiment of the invention relates to a method of enhancing recombinant gene expression by treating a recombinant host cell containing an expression system for a mammalian gene product of interest with an expression-enhancing amount of a compound of Formula I, wherein said gene product is encoded by a butyric acid-responsive gene. The host cells can be mammalian cells, insect cells, yeast cells or bacterial cells and the correspondingly known expression systems for each of these host cells. The gene product can be any protein or peptide of interest expression of which can be regulated or altered by butyric acid or a butyric acid salt. A butyric acid-responsive gene is a gene that has a promoter, enhancer element or other regulon that modulates expression of the gene under its control in response to butyric acid or a salt of butyric acid. For example, gene products contemplated for regulation in accordance with the invention include but are not limited to tumor suppressor genes (such as p53) and the γ-globin chain of fetal hemoglobin.

Yet a further embodiment of the invention is directed to a method of treating, preventing or ameliorating symptoms in insulin-dependent patients by administering an amount of a compound of Formula I effective to enhance insulin expression.

Yet another embodiment of the invention relates to a method of treating, preventing or ameliorating symptoms in cystic fibrosis patients by administering an amount of a compound of Formula I effective to enhance chloride channel expression.

Still another method of the invention is directed to a method of inhibiting telomerase activity in cancer cells by administering a telomerase-inhibiting amount of a compound of Formula I to the cells, wherein the amount is effective to decrease the telomerase activity of the cells and thereby inhibit the malignant progression of the cells. This method can be applied to in vivo or in vitro cells.

Another embodiment of this invention is directed to a method of treating, preventing or ameliorating virus-associated tumors by pre-, post or co-administering a therapeutically-effective amount of a compound of Formula I with a therapeutically-effective amount of an antiviral agent. Antiviral agents contemplated for use in the invention include ganciclovir, acyclovir and famciclovir, and preferably ganciclovir. The virus-associated tumors which can be treated, prevented or ameliorated in accordance with the invention include, but are not limited to, EBV-associated malignancy, Kaposi's sarcoma, AIDS-related lymphoma, hepatitis B-associated malignancy or hepatitis C associated malignancy. EBV-associated malignancies include nasopharyngeal carcinoma and non-Hodgkins' lymphoma and are preferred embodiments of the invention.

Further still the invention is directed to a method of augmenting gene expression, especially of a tumor suppressor gene, a butyric acid-responsive gene or a fetal hemoglobin gene, by treating a host or host cells with an expression-enhancing amount of a compound of Formula I. Preferably the host is a cancer patient. This method of the invention thus includes augmenting tumor suppressor gene expression in conjunction with ex vivo or in vivo gene therapy, i.e., the compound of the invention can be co-administered to the host during administration of gene therapy vectors or administration of the ex vivo transfected cells. Similarly, the compounds of the invention can be used to treat cells during the transfection step of ex vivo gene therapy. The hosts of the method therefore include cancer patients or other patients under going gene therapy. The host cells of the invention include hematopoietic cells such as stem cells and progenitor cells, e.g., or any other cell type used in ex vivo gene therapy.

Yet another embodiment of the invention is directed to a method of inducing tolerance to an antigen which comprises administering a therapeutically-effective amount of compound of Formula I. Preferably the antigen is a self-antigen.

Another aspect of the invention is directed to compounds represented by Formula (II):

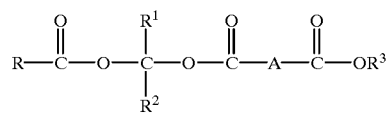

wherein

R is n-propyl, isopropyl, 1-methylpropyl, n-butyl, isobutyl, 1-methylbutyl, 2-methylbutyl, n-amyl, isoamyl, 1-, 2- or 3-methylamyl, 2-ethylbutyl, benzyl, 2-pyridylmethyl, 3-pyridylmethyl, or 4-pyridylmethyl, any of which can be optionally substituted with halo, trifluoromethyl, amino, alkoxy, aryl, or heteroaryl; or R is $C_3$ to $C_5$ linear alkenyl, optionally substituted with halo, trifluoromethyl, amino, alkoxy, aryl, or heteroaryl;

$R^1$ and $R^2$ are independently H, lower alkyl or lower alkenyl;

A is aryl, heteroaryl, or $C_1$ to $C_8$ alkyl, alkenyl, or alkynyl, wherein alkyl, alkenyl and alkynyl are optionally substituted with one or more of hydroxy, halo, lower alkyl, alkoxy, carbonyl, thiol, lower alkylthio, aryl or heteroaryl;

$R^3$ is H, lower alkyl, aryl, or —$CR^1R^2$—O—C(O)—R; and pharmaceutically-acceptable salts thereof.

In a preferred embodiment, the compounds of the invention are those of Formula II, wherein R is n-propyl, 3-(phenyl)propyl, 2-propenyl, benzyl, 2-pyridylmethyl, 3-pyridylmethyl, or 4-pyridylmethyl or 3-(2-, 3- or 4-pyridyl)propyl;

A is $C_1$ to $C_8$ alkyl, alkenyl, or alkynyl, optionally substituted with halo, alkoxy, aryl, substituted aryl, heteroaryl, or substituted heteroaryl;

$R^3$ is H, lower alkyl, or —$CR^1R^2$—O—C(O)—R; and pharmaceutically-acceptable salts thereof.

In a more preferred embodiment, the compounds of the invention are GOMB, bisGOMB, mono-(1-butyroyloxyethyl)glutarate and bis-(1-butyroyloxyethyl) glutarate, and most preferably, GOMB.

Another embodiment of the present invention is drawn to pharmaceutical compositions comprising a therapeutically-effective amount of a compound of Formula (II) and a pharmaceutically-effective carrier or diluent.

A further embodiment of the present invention is directed to pharmaceutical compositions comprising a therapeutically-effective amount of a compound of Formula (II) with a pharmaceutical agent and a pharmaceutically-effective carrier or diluent. The pharmaceutical agents of the invention include but are not limited to cytokines, interleukins, anti-cancer agents, chemotherapeutic agents, antibodies, conjugated antibodies, immune stimulants, antibiotics, hormone antagonists or growth stimulants.

BRIEF DESCRIPTION OF THE DRAWINGS

FIG. 3 is a graphic illustration showing growth inhibition measured by reduction of [$^3$H]-thymidine uptake in EBV-transformed cell line as a function of concentration of ganciclovir (GC)(panel A), GC and AB (panel B) and GC and GOMB (panel C). In panels B and C, the GC concentration is indicated in the inset.

DETAILED DESCRIPTION OF THE INVENTION

Figure 1A:
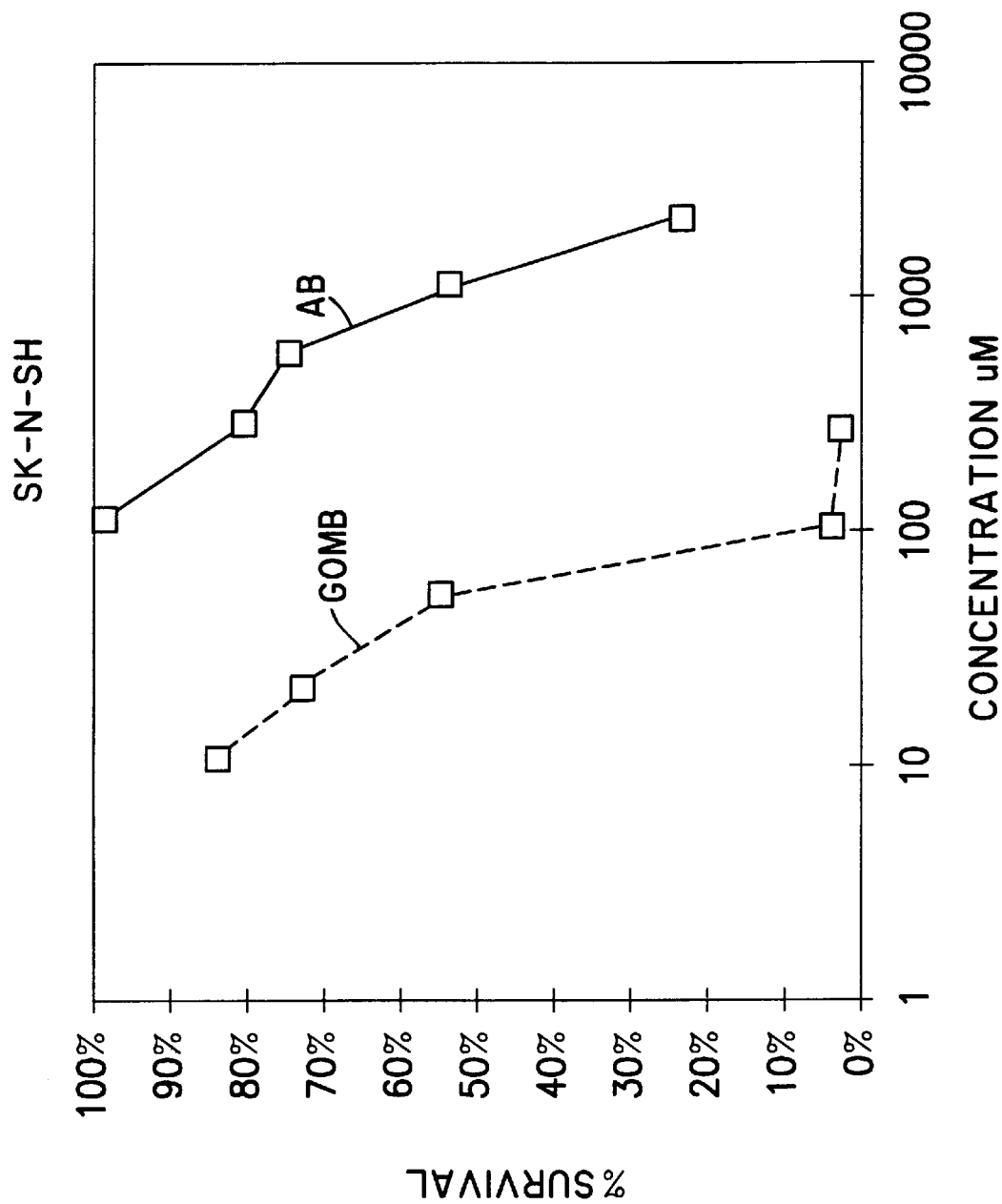
FIG. 1 is a graphic illustration showing the in vitro inhibition of cellular growth (clonogenicity) by GOMB and AB on established human neuroblastoma cell lines as a function of concentration (in $\mu$M).
Figure 1B:
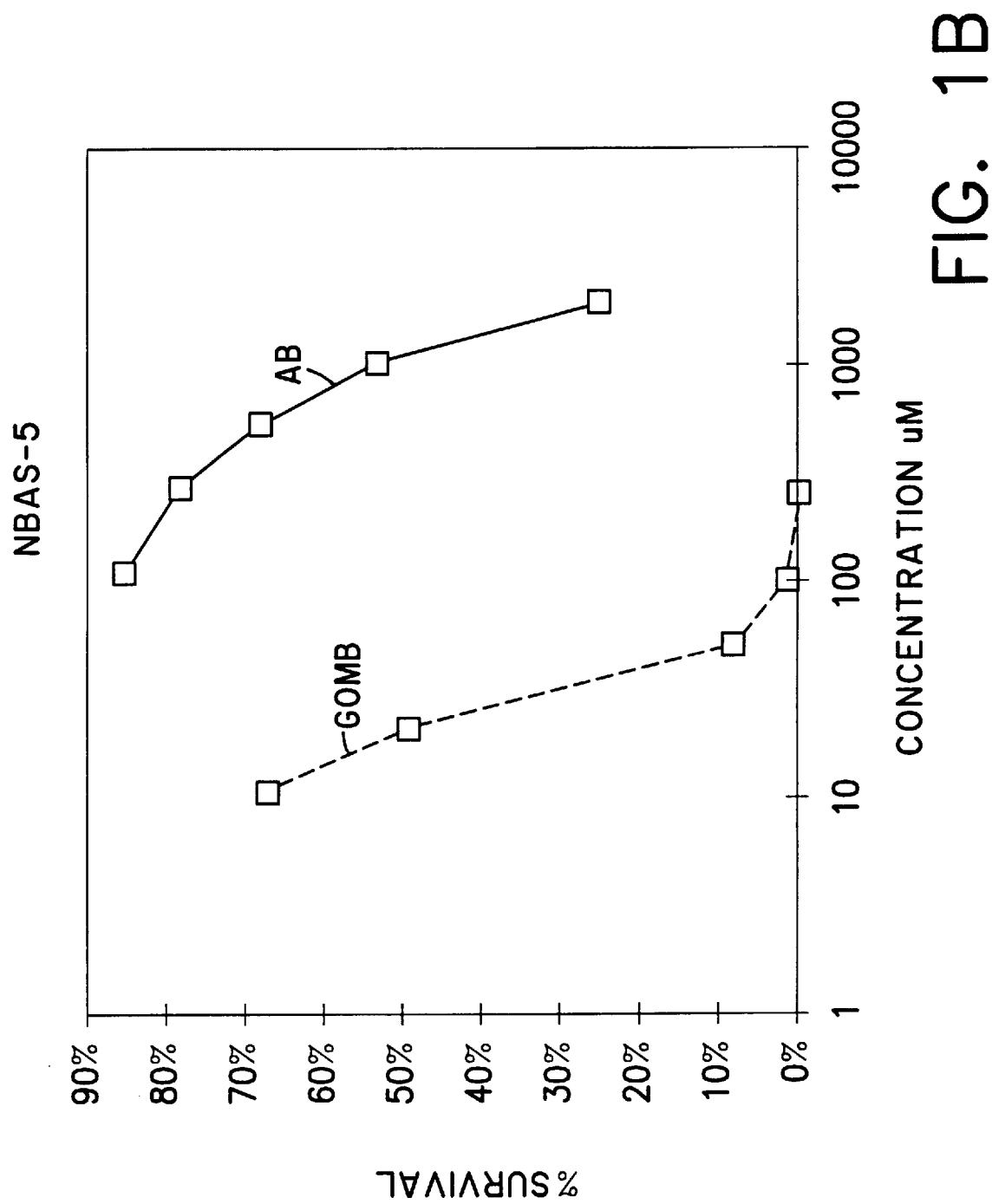
Figure 1C:
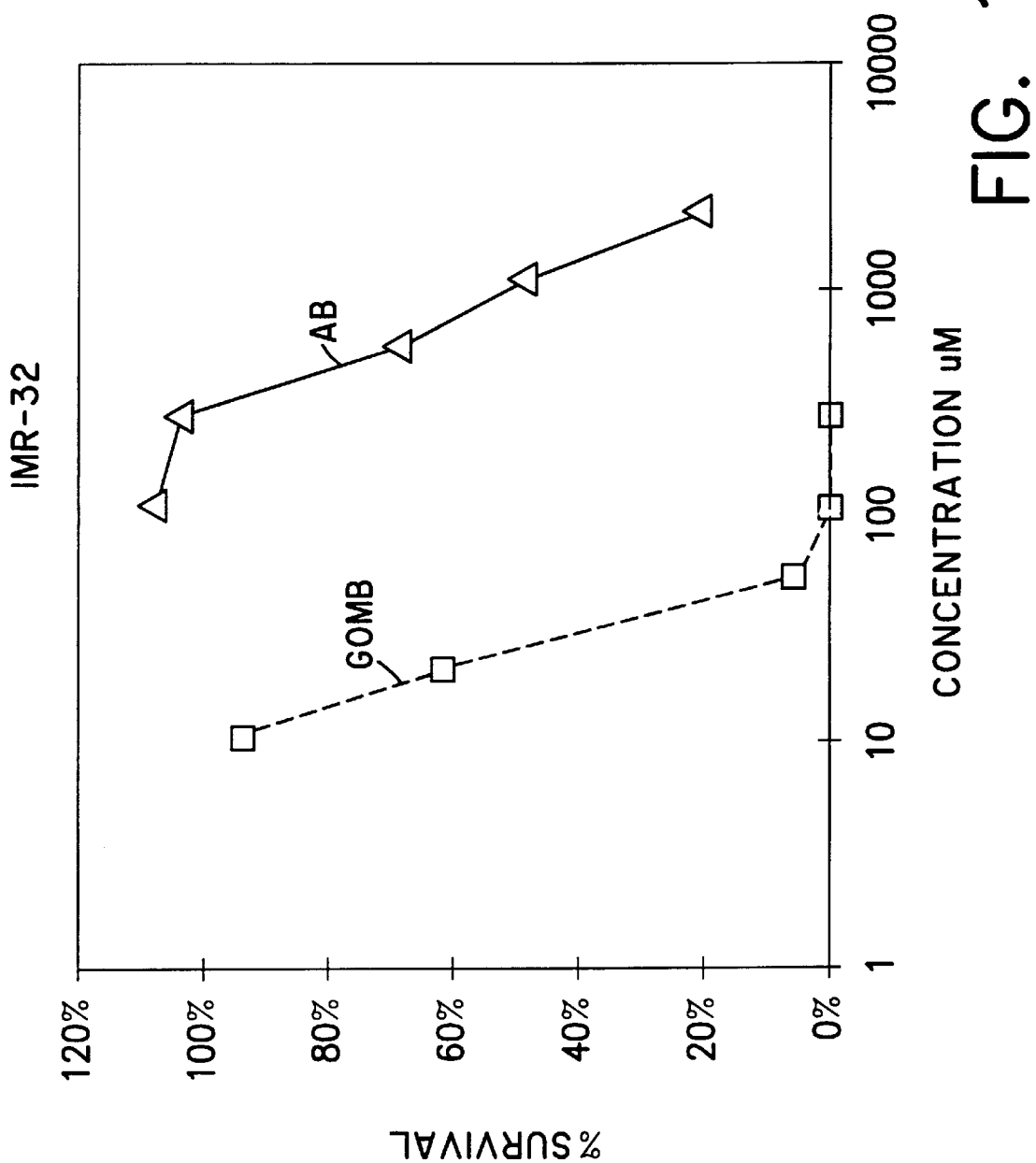
Figure 1D:
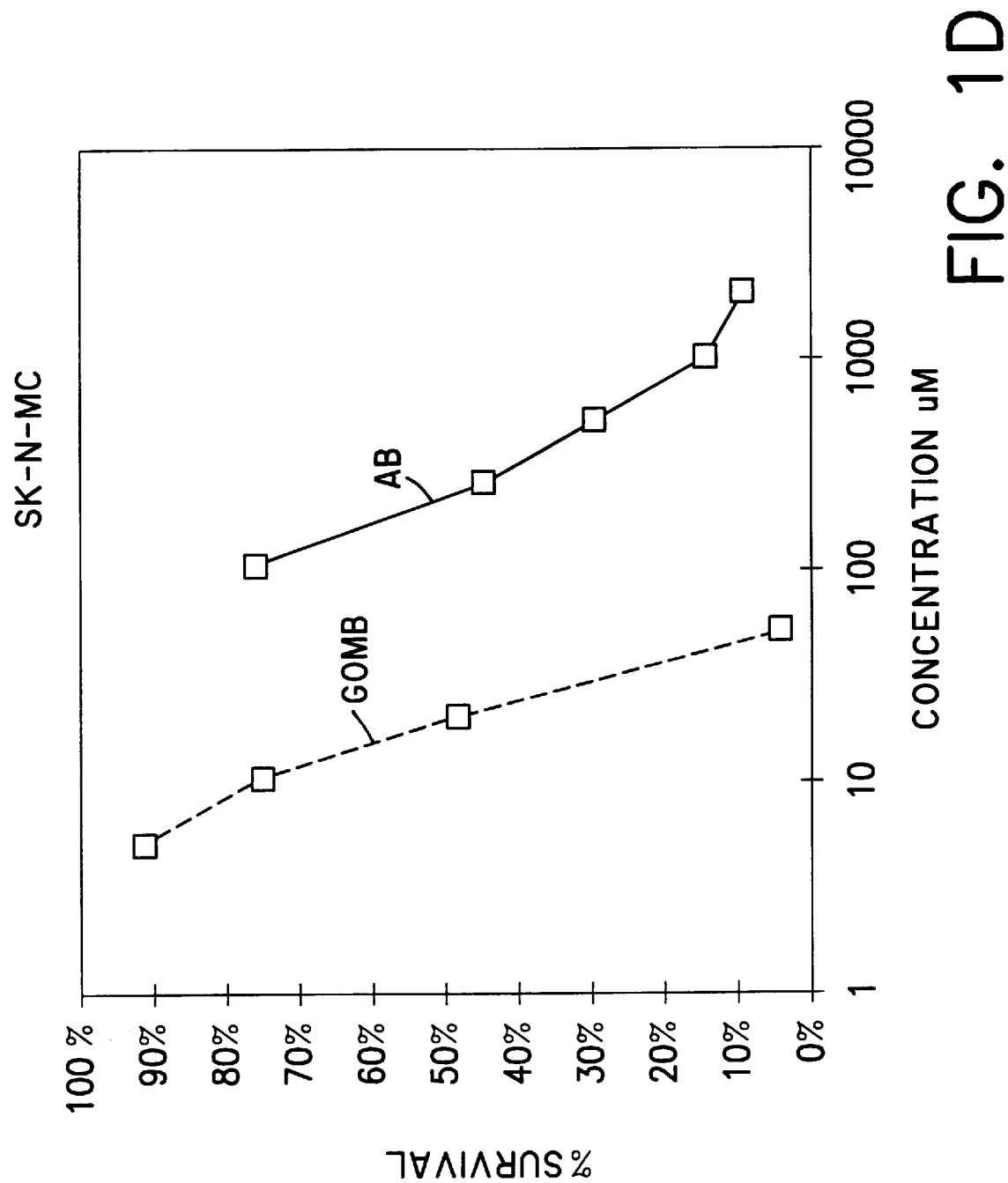

The compounds herein described may have asymmetric centers. All chiral, diastereomeric, and racemic forms are included in the present invention. Many geometric isomers of olefins and the like can also be present in the compounds described herein, and all such stable isomers are contemplated in the present invention.

By "stable compound" or "stable structure" is meant herein a compound that is sufficiently robust to survive isolation to a useful degree of purity from a reaction mixture, and formulation into an efficacious therapeutic agent.

As used herein, "alkyl" means both branched- and straight-chain, saturated aliphatic hydrocarbon groups having the specified number of carbon atoms. As used herein "lower alkyl" means an alkyl group having 1 to 5 carbon atoms. As used herein, "alkenyl" means hydrocarbon chains of either a straight or branched configuration and one or more unsaturated carbon-carbon bonds, such as ethenyl, propenyl, and the like. Lower alkenyl is an alkenyl group having 2 to 6 carbon atoms. As used herein, "alkynyl" means hydrocarbon chains of either a straight or branched configuration and one or more carbon-carbon triple bonds, such as ethynyl, propynyl and the like.

When alkyl, alkenyl, and alkynyl, or a variation thereof such as lower alkyl, are used to define the A moiety of Formulas I and II (or any other group that has two appendages) then these groups have the meanings as defined herein except that each term refers to a hydrocarbon chain having the specified number of carbon atoms. Similarly, when aryl and heteroaryl are used to define the A moiety of Formulas I and II, then these groups have the meanings defined herein except that there are two attachment points on the aromatic ring. When A is an alkyl chain, one preferred A moiety has up to three lower alkyl substituents and, even more preferably, up to three methyl groups.

As used herein, "aryl" includes "aryl" and "substituted aryl." Thus "aryl" of this invention means any stable 6- to 14-membered monocyclic, bicyclic or tricyclic ring, containing at least one aromatic carbon ring, for example, phenyl, naphthyl, indanyl, tetrahydronaphthyl (tetralin) and the like, optionally substituted with halo, alkyl, alkoxy, hydroxy, carboxy, cyano, nitro, amino or acylamino.

As used herein, the term "heteroaryl" includes "heteroaryl" and "substituted heteroaryl." Thus "heteroaryl" of this invention means a stable 5- to 10-membered monocyclic or bicyclic heterocyclic ring which is aromatic, and which consists of carbon atoms and from 1 to 3 heteroatoms selected from the group consisting of N, O and S and wherein the nitrogen may optionally be quaternized, and including any bicyclic group in which any of the above-defined heteroaryl rings is fused to a benzene ring. The heteroaryl ring may be attached to its pendant group at any heteroatom or carbon atom which results in a stable structure. The heteroaryl rings described herein may be optionally substituted on carbon, on a nitrogen atom or other heteroatom if the resulting compound is stable and all the valencies of the atoms have been satisfied. The substituents of the substituted heteroaryl groups are as for the substituted aryl groups (see above). Examples of heteroaryl groups include, but are not limited to, pyridyl, pyrimidinyl, furanyl, thienyl, pyrrolyl, pyrazolyl, imidazolyl, tetrazolyl, benzofuranyl, benzothienyl, indolyl, indolenyl, quinolinyl, isoquinolinyl and benzimidazolyl.

As used herein and in the claim, "aralkyl", and "heteroaralkyl" refer to an aryl or heteroaryl group, respectively, as described above attached to an alkyl group as described above. Examples of heteroaralkyl groups include but are not limited to 2-, 3-, or 4-pyridylmethyl and 3-(2-, 3- or 4-pyridyl)propyl and the like.

The term "substituted", as used herein, means that one or more hydrogens on the designated atom are replaced with a selection from the indicated substituents, provided that the designated atom's normal valency is not exceeded, and that the substitution results in a stable compound.

The substituents of the invention include, as indicated, halo, hydroxy, alkyl, alkoxy, amino, acylamino, carboxy, carbonyl, cyano, nitro, and trifluoromethyl groups. These groups can be substituents for alkyl, alkenyl, alkynyl, aryl, aralkyl, heteroaryl, heteroaralkyl, and saturated heterocyclic groups as indicated in accordance with the invention. A halo group is a halogen, and includes fluoro, chloro, bromo and iodo groups. The alkyl moiety of alkoxy, acyl, aralkyl, heteroaralkyl and the like is lower alkyl unless otherwise specified.

As used herein, "therapeutically-effective amount" refers to that amount necessary to administer to a host to achieve an anti-tumor effect; to induce differentiation and/or inhibition of proliferation of malignant cancer cells, benign tumor cells or other proliferative cells; to aid in the chemoprevention of cancer; to promote wound healing; to treat a gastrointestinal disorder; to treat a blood disorder or increase the hemoglobin content of blood; to modulate an immune response; to enhance gene expression; to augment expression of tumor suppressor genes; to enhance insulin expression; to enhance chloride channel expression or to induce tolerance to an antigen. Methods of determining therapeutically-effective amounts are well known.

As used herein, "pharmaceutically acceptable salts" refer to derivatives of the disclosed compounds that are modified by making acid or base salts. Examples include, but are not limited to, mineral or organic acid salts of basic residues such as amines; alkali or organic salts of acidic residues such as carboxylic acids, and the like.

Pharmaceutically-acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. The salts of the invention can also be prepared by ion exchange, for example. Lists of suitable salts are found in *Remington's Pharmaceutical Sciences,* 17th ed., Mack Publishing Company, Easton, Pa., 1985, p. 1418, the disclosure of which is hereby incorporated by reference in its entirety.

The "pharmaceutical agents" for use in the methods of the invention related to the coadministration of compounds of Formula I and Formula II, include but are not limited to anticancer agents as well as differentiating agents. For example, the pharmaceutical agent can be a cytokine, an interleukin, an anti-cancer agent or anti-neoplastic agent, a chemotherapeutic agent, an antibody, a conjugated antibody, an immune stimulant, an antibiotic, a hormone antagonist or a growth stimulant. The pharmaceutical agent can also be a cytotoxic agent. Cytotoxic agents include antiviral nucleoside antibiotic such as ganciclovir, acyclovir, and famciclovir.

As used herein, the "chemotherapeutic agents" include but are not limited to alkylating agents, purine and pyrimidine analogs, vinca and vinca-like alkaloids, etoposide and etoposide-like drugs, corticosteroids, nitrosoureas, antimetabolites, platinum-based cytotoxic drugs, hormonal antagonists, anti-androgens and antiestrogens.

The "cytokines" for use herein include but are not limited to interferon, preferably α, β or γ interferon, as well as IL-2, IL-3, G-CSF, GM-CSF and EPO.

As used herein, an "immune stimulant" is a substance such as *C. parvum* or sarcolectin which stimulates a humoral or cellular component of the immune system.

The chemotherapeutic agents of the invention include but are not limited to tamoxifen, doxorubicin, 1-asparaginase, decarbazine, amacrine, procarbazine, hexamethylmelamine, mitosantrone and gemcitabine.

Synthetic Methods

The compounds of the present invention can generally be prepared by any method known in the art. For example, the compounds of the invention can be made by reacting the acid form of the RCOOH with a reagent of the formula

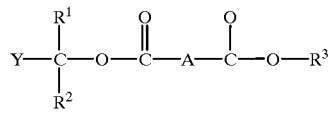

or by similar reactions between any of the appropriate acids and the appropriate alkyl halides, in the presence of a base, where Y is a leaving group such as halogen, methane sulfonate or p-toulenesulfonate and R, $R^1$, $R^2$ and $R^3$ are as defined herein. The above reagents are readily prepared according to literature procedures, see for example, Nudelman et al., *J. Med. Chem.* 35:687–694, 1992, and Japanese patent 07033709 (1995). The base can be a trialkylamine, pyridine, an alkali metal carbonate or other suitable base. The reaction can be carried out in the presence or absence of an inert solvent. Suitable solvents include, for example, acetone, benzene, toluene, tetrahydrofuran, ethyl acetate, acetonitrile, dimethylformamide, dimethyl sulfoxide, chloroform, dioxan or 1,2-dichloroethane.

The procedures outlined above can be improved by one skilled in the art by, for instance, changing the temperature, duration, stoichiometry or other parameters of the reactions. Any such changes are intended to fall within the scope of this invention.

Activity

The activities of the compounds of the invention can be measured using generally-accepted techniques known to those skilled in the art consistent with the activity of interest. For example, the activity of compounds useful as differentiating agents can be measured using standard methodology of the nitro-blue tetrazolium reduction assay (e.g., Rabizadeh et al., *FEBS Lett.* 328:225–229, 1993; Chomienne et al., *Leuk. Res.* 10:631, 1986; and Breitman et al. in *Methods for Serum-free Culture of Neuronal and Lymphoid Cells*, Alan R. Liss, New York, p. 215–236, 1984 which are hereby incorporated by reference in their entirety) and as described below. This in vitro assay has been deemed to be predictive and in fact correlative with in vivo efficacy (Castaigne et al., *Blood* 76:1704–1709, 1990).

Another assay which is predictive of differentiating activity is the morphological examination for the presence of Auer rods and/or specific differentiation cell surface antigens in cells collected from treatment groups, as described in Chomienne et al., (*Blood* 76:1710–1717, 1990 which is hereby incorporated by reference in its entirety) and as described below.

The compounds of the present invention also have antiproliferative and anti-tumor activity. The anti-proliferation activity of compounds of the present invention can be determined by methods generally known to those skilled in the art. Generally-accepted assays for measuring viability and anti-proliferative activity are the trypan blue exclusion test and incorporation of tritiated thymidine, also as described by Chomienne, et al., above, which is incorporated herein by reference. Other assays which predict and correlate antitumor activity and in vivo efficacy are the human tumor colony forming assay described in Shoemaker et al., *Can. Res.* 45:2145–2153, 1985, and inhibition of telomerase activity as described by Hiyayama et al., *J. Natl. Cancer Inst.* 87:895–908, 1995, which are both incorporated herein by reference in their entirety. These assays are described in further detail below.

Cell Cultures

Human promyelocytic leukemia cells (HL-60), human pancreatic carcinoma cells (PaCa-2) and human breast adenocarcinoma cells, pleural effusion cells (MCF-7) can be cultured as follows. Cells are grown in RPMI media with 10% FCS, supplemented with 2 mM glutamine and incubated at 37° C. in a humidified 5% $CO_2$ incubator. Alternatively, cells can be grown in any other appropriate growth medium and conditions which supports the growth of the cell line under investigation. Viability can be determined by trypan blue exclusion. Cells are exposed to a test compound, cultures are harvested at various time points following treatment and stained with trypan blue.

Cellular Staining to Detect Differentiation

Lipid staining and/or immunochemical staining of casein can be used as a marker for cellular differentiation of breast cancer cells (Bacus et al., *Md. Carcin.* 3:350–362, 1990). Casein detection can be done by histochemical staining of breast cancer cells using a human antibody to human casein as described by Cheung et al., *J. Clin. Invest.* 75:1722–1728, which is incorporated by reference in its entirety.

Nitro-Blue Tetrazolium (NBT) Assay

Cell differentiation of myeloid leukemia cells can be evaluated, for example, by NBT reduction activity as follows. Cell cultures are grown in the presence of a test compound for the desired time period. The culture medium is then brought to 0.1% NBT and the cells are 21 stimulated with 400 mM of 12-O-tetradecanoyl-phorbol-13-acetate (TPA). After incubation for 30 min at 37° C., the cells are examined microscopically by scoring at least 200 cells. The capacity for cells to reduce NBT is assessed as the percentage of cells containing intracellular reduced black formazan deposits and corrected for viability.

Cell Surface Antigen Immunophenotyping

Cell surface antigen immunotyping can be conducted using dual-color fluorescence of cells gated according to size. The expression of a panel of antigens from early myeloid (CD33) to late myeloid can be determined as described in Warrell, Jr. et al., *New Engl. J. Med.* 324:1385–1392, 1992, which is incorporated by reference herein in its entirety.

Apoptosis Evaluation

Apoptosis can be evaluated by DNA fragmentation, visible changes in nuclear structure or immunocytochemical analysis of Bcl-2 expression.

DNA fragmentation can be monitored by the appearance of a DNA ladder on an agarose gel. For example, cellular DNA is isolated and analyzed by the method of Martin et al., *J. Immunol.,* 145:1859–1867, 1990 which is incorporated by reference herein in its entirety.

Changes in nuclear structure can be assessed, for example, by acridine orange staining method of Hare et al., *J. Hist. Cyt.,* 34:215–220, 1986 which is incorporated by reference herein in its entirety.

Immunological detection of Bcl-2 can be performed on untreated cells and cells treated with the test compound. HL-60 cells are preferred but other cell lines capable of expressing Bcl-2 can be used. Cytospins are prepared and the cells are fixed with ethanol. Fixed cells are reacted overnight at 4° C. with the primary monoclonal antibody, anti-Bcl-2 at a dilution of 1:50. Staining is completed to visualize antibody binding, for example, using Strep A-B Universal Kit (Sigma) in accordance with the manufacturer's instructions. Identically-treated cells which received no primary antibody can serve as a non-specific binding control. Commercial kits are also available and can be used for detecting apoptosis, for example, Oncor's Apop Tag®.

Modulation of Gene Expression

The levels of expression from oncogene and tumor suppressor genes can be evaluated by routine methods known in the art such as Northern blotting of RNA, immunoblotting of protein and PCR amplification.

Mouse Cancer Model

Compounds can be examined for their ability to increase the life span of animals bearing B16 melanomas, Lewis lung carcinomas and myelomonocytic leukemias as described in Nudelman et al., *J. Med. Chem.* 35:687–694, 1992, or Rephaeli et al., *Int. J. Cancer* 49:66–72, 1991, which are incorporated by reference herein in their entireties.

For example, the efficacy of compounds of the present invention in a leukemia model can be tested as follows: Balb/c mice are injected with WEHI cells and a test compound or control solution is administered the following day. The life span of the treated animals is compared to that of untreated animals.

The efficacy of compounds of the present invention on primary tumors can also be tested with subcutaneously implanted lung carcinoma or B16 melanoma by measuring the mass of the tumor at the site of implantation every two weeks in control and treated animals.

The efficacy of compounds in xenografts can be determined by implanting the human tumor cells subcutaneously into athymic mice. Human tumor cell lines which can be used include, but are not limited to, prostate carcinoma (human Pc-3 cells), pancreatic carcinoma (human Mia PaCa cells), colon adenocarcinoma (human HCT-15 cells) and mammary adenocarcinoma (human MX-1 cells). Treatment with control solution or a test compound of the invention begins, for example, when tumors are approximately 100 mg. Anti-tumor activity is assessed by measuring the delay in tumor growth, and/or tumor shrinking and/or increased survival of the treated animals relative to control animals.

Telomerase Activity

High levels of telomerase activity is associated with the high proliferation rate found in cancer cells. Compounds which inhibit telomerase activity results in inhibition of cancer cell growth and de-differentiation. Commercially available telomerase assays can thus be used to assess the anticancer activities of compounds on cancer cell lines.

Chemoprevention

The chemoprevention activity of the compounds of the invention can be determined in the two-stage mouse carcinogenesis model of Nishimo et al. (supra).

Assay of Compounds

Compounds of the invention, their salts or metabolites, can be measured in a biological sample by any method known to those skilled in the art of pharmacology, clinical chemistry or the like. Such methods for measuring these compounds are standard methods and include, but are not limited to high performance liquid chromatography (HPLC), gas chromatography (GC), gas chromatography mass spectroscopy (GC-MS), radioimmunoassay (RIA), and others.

Dosage and Formulation

The compounds of the present invention can be administered to a mammalian patient to treat cancer or in any other method of the invention which involves treating a patient by any means that produces contact of the active agent with the agent's site of action in the body of the subject. Mammalian patients include humans and domestic animals. The compounds of the invention can be administered by any conventional means available for use in conjunction with pharmaceuticals, either as individual therapeutic agents or in a combination of therapeutic agents. The compounds can be administered alone, but are generally administered with a pharmaceutical carrier selected on the basis of the chosen route of administration and standard pharmaceutical practice. The pharmaceutical compositions of the invention may be adapted for oral, parenteral, transdermal, transmucosal, rectal or intranasal administration, and may be in unit dosage form, as is well known to those skilled in the pharmaceutical art. The term "parenteral" as used herein includes subcutaneous, intravenous, intramuscular, or intrasternal injection or infusion techniques.

The appropriate dosage administered in any given case will, of course, vary depending upon known factors, such as the pharmacodynamic characteristics of the particular agent and its mode and route of administration; the age, general health, metabolism, weight of the recipient and other factors which influence response to the compound; the nature and extent of the symptoms; the kind of concurrent treatment; the frequency of treatment; and the effect desired. A daily dosage of active ingredient can be expected to be about 10 to 10,000 milligrams per meter$^2$ of body mass (mg/m$^2$), with the preferred dose being 50–5,000 mg/M$^2$ body mass.

Dosage forms (compositions suitable for administration) contain from about 1 mg to about 1 g of active ingredient per unit. In these pharmaceutical compositions the active ingredient will ordinarily be present in an amount of about 0.5–95% by weight based on the total weight of the composition.

The active ingredient can be administered orally in solid or semi-solid dosage forms, such as for example hard or soft-gelatin capsules, tablets, and powders, or in liquid dosage forms, such as elixirs, syrups, disperse powders or granules, emulsions, and aqueous or oily suspensions. It can also be administered parenterally, in sterile liquid dosage forms. Other dosage forms include transdermal administration via a patch mechanism or ointment.

Compositions intended for oral use may be prepared according to any methods known to the art for the manufacture of pharmaceutical compositions and such compositions may contain one or more agents including sweetening agents, flavoring agents, coloring agents, and preserving agents in order to provide a pharmaceutically elegant and palatable preparation.

Tablets contain the active ingredient in admixture with non-toxic pharmaceutically acceptable excipients which are suitable for the manufacture of tablets. Such excipients may include, for example, inert diluents, such as calcium phosphate, calcium carbonate, sodium carbonate, sodium phosphate, or lactose; granulating disintegrating agents, for example, maize starch or alginic acid; binding agents, such as starch, gelatin, or acacia; and lubricating agents, for example, magnesium stearate, stearic acids or talc. Compressed tablets may be uncoated or may be sugar coated or film coated by known techniques to mask any unpleasant taste and protect the tablet from the atmosphere, or enteric coated for selective disintegration and adsorption in the gastrointestinal tract.

Hard gelatin capsules or liquid filled soft gelatin capsules contain the active ingredient and inert powdered or liquid carriers, such as, but not limited to calcium carbonate, calcium phosphate, kaolin, lactose, lecithin starch, cellulose derivatives, magnesium stearate, stearic acid, arachis oil, liquid paraffin, olive oil, pharmaceutically-accepted synthetic oils and other diluents suitable for the manufacture of capsules. Both tablets and capsules can be manufactured as sustained release-products to provide for continuous release of medication over a period of hours.

Aqueous suspensions contain the active compound in admixture with excipients suitable for the manufacture of aqueous suspensions. Such excipients are suspending agents, e.g., sodium carboxymethylcellulose, methylcellulose, hydroxypropylmethylcellulose, sodium alginate, polyvinylpyrrolidone, gum tragacanth, and gum acacia; dispersing or wetting agents, such as a naturally occurring phosphatide, e.g., lecithin, or condensation products of an alkylene oxide with fatty acids, for example polyoxyethylene stearate, or a condensation products of ethylene oxide with long chain aliphatic alcohols, e.g., heptadecaethyleneoxycetanol, or condensation products of ethylene oxide with partial esters derived from fatty acids and a hexitol, e.g., polyoxyethylene sorbitol monooleate, or a condensation product of ethylene oxide with partial esters derived from fatty acids and hexitol anhydrides, e.g., polyoxyethylene sorbitan monooleate. The aqueous suspensions can also contain one or more preservatives, for example ethyl, n-propyl, or p-hydroxy benzoate, one or more coloring agents, one or more flavoring agents, and one or more sweetening agents, such as sucrose, saccharin, or sodium or calcium cyclamate.

Dispersable powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents, can also be present.

Syrups and elixirs can be formulated with sweetening agents, such as glycerol, sorbitol or sucrose. Such formulations may also contain a demulcent, a preservative and flavoring and coloring agents.

The pharmaceutical compositions can be in the form of a sterile injectable preparation, for example, as a sterile injectable aqueous suspension. This suspension can be formulated according to the known art using those suitable dispersing or wetting agents and suspending agents which have been mentioned above. The sterile injectable preparation can also be a sterile injectable solution or suspension in a nontoxic parenterally-acceptable diluent or solvent, for example, as a solution in 1,3-butane diol.

In general, water, a suitable oil, saline, aqueous dextrose (glucose), polysorbate and related sugar solutions, emulsions, such as Intralipid® (Cutter Laboratories, Inc., Berkley Calif.) and glycols such as propylene glycol or polyethylene glycols are suitable carriers for parenteral solutions. Antioxidizing agents, such as but not limited to sodium bisulfite, sodium sulfite, or ascorbic acid, either alone or combined, are suitable stabilizing agents. Also used can be citric acid and its salts and sodium EDTA. In addition, parenteral solutions can contain preservatives, such as but not limited to benzalkonium chloride, methyl- or propyl-paraben, and chlorobutanol.

The pharmaceutical compositions of the present invention also include compositions for delivery across cutaneous or mucosal epithelia including transdermal, intranasal, sublingual, buccal, and rectal administration. Such compositions may be part of a transdermal device, patch, topical formulation, gel, etc., with appropriate excipients. Thus, the compounds of the present invention can be compounded with a penetration-enhancing agent such as 1-n-dodecylazacyclopentan-2-one or the other penetration-enhancing agents disclosed in U.S. Pat. Nos. 3,991,203 and 4,122,170 which are hereby incorporated by reference in their entirety to describe penetration-enhancing agents which can be included in the transdermal or intranasal compositions of this invention.

Suitable pharmaceutical carriers are described in Remington's Pharmaceutical Sciences, Mack Publishing Company, a standard reference text in this field, which is incorporated herein by reference in its entirety.

Various modifications of the invention in addition to those shown and described herein will be apparent to those skilled in the art from the foregoing description. Such modifications are also intended to fall within the scope of the appended claims.

The foregoing disclosure includes all the information deemed essential to enable those skilled in the art to practice the claimed invention. Because the cited patents or publications may provide further useful information these cited materials are hereby incorporated by reference in their entirety.

EXAMPLE 1

Synthesis of GOMB and bis-GOMB

GOMB has the following structure

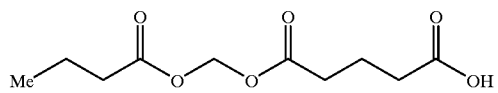

and was synthesized as follows. To a stirred solution of chloromethyl butyrate (8.16g, 60 mmol) in acetone (50 mL), glutaric acid (7.9 g, 60 mmol) was added, followed by the dropwise addition of triethylamine (16 mL, 11.6 g, 120 mmol). The reaction mixture was heated at 70° C. for 2 h, and was further stirred at room temperature for 60 h, after which a large amount of precipitate was obtained. The precipitate was filtered, washed with acetone and the filtrate was partitioned between water (20 mL) and ethyl acetate (20 mL). The aqueous phase was brought to pH 8 with 1 M $K_2CO_3$ and washed with ethyl acetate. The organic phase was extracted 3 more times with basic water (pH 8), and the washings were added to the aqueous phase. The washed organic phase (Solution A) was saved for isolation of bisGOMB. The combined aqueous phase was acidified with 2M HCl and extracted with ethyl acetate (4×20 mL). This second organic phase was collected, dried and evaporated to give the crude residue (3.44 g) which was dissolved in chloroform, washed with water and evaporated to give the pure GOMB, 3 g (22% yield).

To prepare bisGOMB, Solution A was dried and evaporated to give an oily residue(76 g) of crude bisGOMB. This residue was Kugelrohr distilled (190° C./0.5 mm Hg) to give 70 g (0.20 moles, 20% yield) of pure bisGOMB.

The compounds of Table 1 are those of Formula I having the specified groups and can be synthesized in a manner similar to that described above using the appropriate reagents.

TABLE 1

Additional Formula I Compounds of the Invention

| R | $R^1$ | $R^2$ | A | $R^3$ |
|---|---|---|---|---|
| n-$C_3H_7$— | $CH_3$ | H | —$CH_2$—CH($CH_3$)—$CH_2$— | —$C_2H_5$ |
| n-$C_3H_7$— | $CH_3$ | H | —$CH_2$—CH($CH_3$)—$CH_2$— | —$CH_2$—CH($CH_3$)—$CH_2$— |
| $C_6H_5(CH_2)_3$— | $CH_3$ | $CH_3$ | —$CH_2$—$CH_2$— | —H |
| 4-Cl$C_6H_4$— | H | H | —CH=CH— | —$CH_3$ |
| 2-pyridyl | H | H | —CH($CH_3$)—CH($CH_3$)—$CH_2$— | —H |
| 3-pyridyl | H | H | —CH($CH_3$)—CH($CH_3$)—$CH_2$— | —$CH_2$—O—C(=O)—$C_3H_7$ |
| $CH_3$—CH(O$CH_3$)—$CH_2CH_2$— | H | H | —$CH_2$C≡C—$CH_2$— | —H |
| $CH_3$—CH(Br)$CH_2$— | $CH_3$ | $C_2H_5$ | —$(CH_2)_8$— | —$CH_3$ |
| Cl$CH_2CH_2$— | H | H | —$CH_2$—CH(O$CH_3$)—$CH_2$— | —$C_6H_5$ |
| $CH_2$=CH$CH_2$— | H | $CH_3$ | —$(CH_2)_3$— | —H |
| $CH_3$—CH=$CH_2$— | n-$C_3H_7$ | H | —$C_6H_4$— | H |

TABLE 1-continued

Additional Formula I Compounds of the Invention

| R | R¹ | R² | A | R³ |
|---|---|---|---|---|
| n-C$_3$H$_7$— | CH$_3$ | H | (2,3-dimethylphenyl) | —CH(CH$_3$)—OC(=O)—C$_3$H$_7$ |
| C$_6$H$_5$CH$_2$— | C$_4$H$_9$ | H | (2,5-dimethylfuran) | —CH(C$_4$H$_9$)—O—C(=O)CH$_2$C$_6$H$_5$ |

EXAMPLE 2

Clonogenicity of Established Tumor Cell Lines

Inhibition of tumor growth was tested using cell lines as follows:

The cell lines listed in Table 2 were grown to 70–80% confluence in complete media. Cells were harvested, washed in complete media, and counted. Cell viability was determined by trypan blue exclusion. The cells were placed into soft agar (0.12% in media) and plated at 5,000 viable cells per well onto an agarose underlayer (0.4%) in 24-well plates. After overnight culture, AB or GOMB was added at the indicated concentration. Control cells received media alone. As a control for cell death, cells were treated with a superlethal dose of 10 μg/ml of cisplatin. The dosage of AB or GOMB which inhibited fifty percent (or ninety percent) of cell proliferation (IC$_{50}$ or IC$_{90}$) was calculated using the Chou Analysis' Median Effective Dose equation.

The clonogenicity is determined as the percentage of clones in treated cultures relative to clones in media-treated controls cultures. A representative clonogenicity titration curve for AB and GOMB is shown with four neuroblastoma cell lines in FIG. 1. The IC$_{50}$ and IC$_{90}$ values of GOMB and AB for cancer cell lines are provided in Table 3.

The results demonstrate that GOMB is more a potent growth inhibitor than AB. The data show that GOMB and AB inhibit cell proliferation in a dose-dependent manner but that the cells are an order of magnitude more sensitive to GOMB. The ratio of IC$_{50}$ AB:IC$_{50}$ GOMB ranges between 6- to 460-fold with a median of 28.5 μM. Similarly the ratio of IC$_{90}$ AB:IC$_{90}$ GOMB ranges between 26–342-fold with a median value of 53 μM. The IC$_{90}$ values are clinically important for assessing eradication of residual cancer disease.

TABLE 2

Human Tumor Cell Lines

| Cell Lines | Origin |
|---|---|
| MCF7-WT | Breast Carcinoma |
| MCF7-40F | Breast Carcinoma |
| PC3 | Prostate Carcinoma |
| LNCaP | Prostate Carcinoma |
| K562 | Erytholeukemia |
| SK-N-SH | Neuroblastoma |
| NBAS-5 | Neuroblastoma |

TABLE 2-continued

Human Tumor Cell Lines

| Cell Lines | Origin |
|---|---|
| IMR-32 | Neuroblastoma |
| LA1-5S | Neuroblastoma |
| NBL-W-N | Neuroblastoma |
| SMS-KAN | Neuroblastoma |
| SK-N-MC | Neuroblastoma |

TABLE 3

Inhibition of Established and Primary Tumor Cell Lines by AB and GOMB

| | AB | | GOMB | | AB/GOMB | |
| | | | | | IC$_{50}$ | IC$_{90}$ |
| Cell Line | IC$_{50}$[a] | IC$_{90}$ | IC$_{50}$ | IC$_{90}$ | Ratio | Ratio |
|---|---|---|---|---|---|---|
| MCF7-WT | 1500 | 9473 | 43.5 | 97 | 34.5 | 97.7 |
| MCF7-40F | 817 | 3183 | 65.9 | 85.3 | 12.4 | 37.3 |
| PC3 | 226 | 447 | 34.9 | 96.1 | 6.48 | 46.6 |
| LNCaP | 780 | 6703 | 68.1 | 107 | 11.4 | 63 |
| K562 | 772 | 665 | 43.3 | 97 | 17.8 | 68.6 |
| SK-N-SH | 998 | 3397 | 28 | 95 | 35.6 | 37.8 |
| NBAS-5 | 883 | 13030 | 16 | 38 | 23.2 | 343 |
| SK-N-MC | 215 | 1314 | 16 | 35 | 13.4 | 37.5 |
| IMR-32 | 881 | 3566 | 23 | 41 | 38 | 87 |
| LA1-5S | 1627 | 2675 | 39 | 59 | 42 | 45 |
| NBL-W-N | 489 | 3074 | 25 | 70 | 19.6 | 44 |
| SMS-KAN | 1138 | 2079 | 27 | 80 | 42 | 26 |
| Primary[b] | 4645 | 2120 | 34 | 78 | 13.9 | 27.3 |

[a]All concentrations are in μM.
[b]Data from 53 primary tumor cell lines treated with AB and GOMB as described in Example 3.

EXAMPLE 3

Inhibition of Clonogenicity of Primary Tumor Cells

Figure 2:
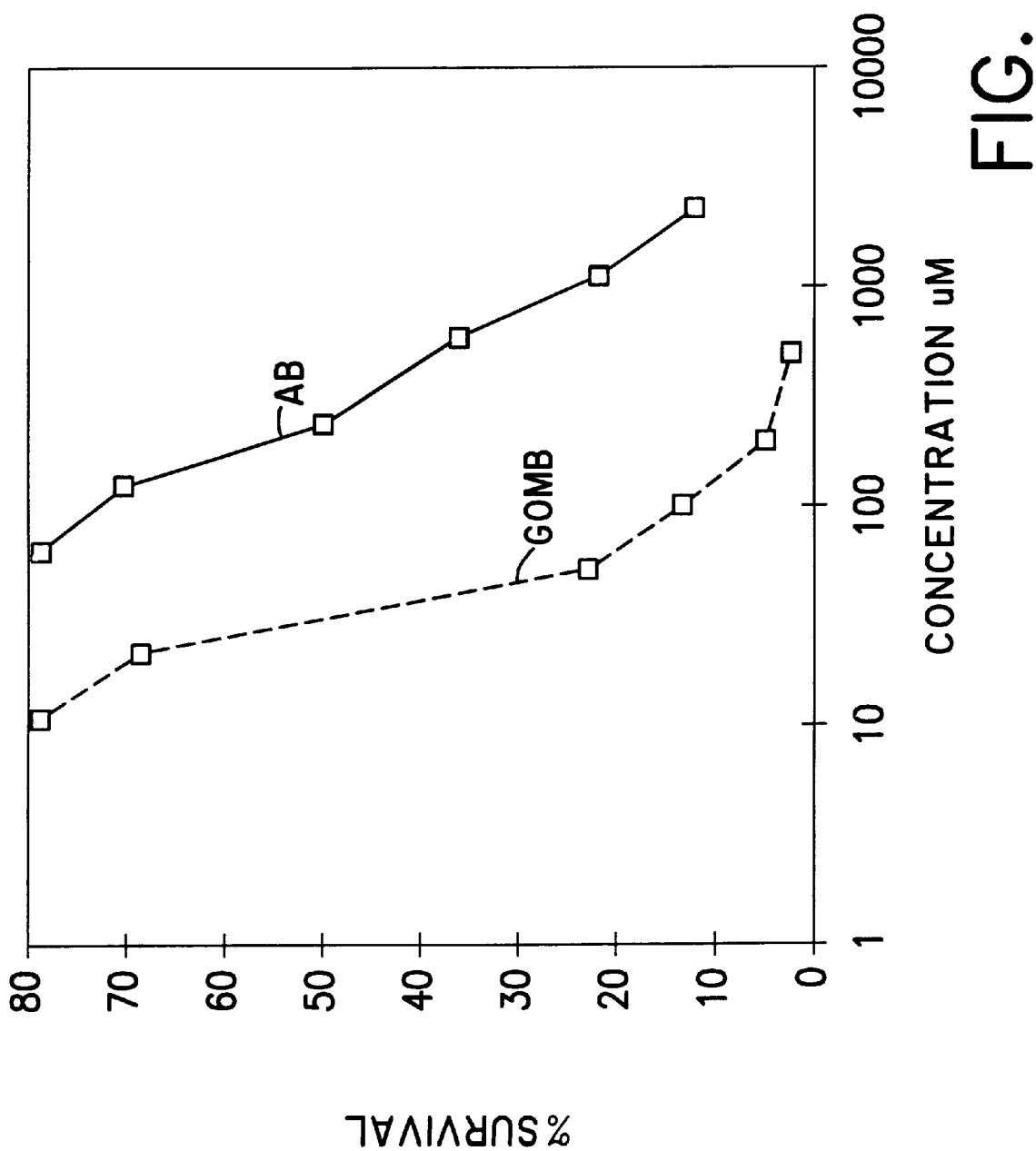
FIG. 2 is a graphic illustration showing the average in vitro inhibition of growth by GOMB and AB on 53 primary human tumor cells as a function of concentration (in $\mu$M).

The effect of GOMB was compared to that of AB on a variety of primary tumor cells as described in Example 2, except that,cells were seeded at 30,000 cells per well. The average IC50 value, IC$_{90}$ value, AB/GOMB IC$_{50}$ ratio and AB/GOMB IC90 ratio are provided in Table 3. The tested tumor cells were from 11 non-small cell lung carcinomas, 10 breast carcinomas, 10 gastric carcinomas, 10 ovarian carcinomas, and 10 CNS tumors. FIG. 2 shows the average tumor cell clonogenicity as a function of AB and GOMB for all 53 lines of tumor cells; GOMB is a more potent inhibitor of cell proliferation than is AB.

EXAMPLE 4

Synergy of AB and GOMB with Antiviral Agent

The effect of GOMB to AB was compared on EBV virus-associated tumors. EBV-positive cells from P3HR-1, a human lymphoma cell line, were incubated in growth medium with the specified concentration of GOMB, AB, ganciclovir (GC), or combination of these, for 72 hours, seeded in 96-well plates and pulsed with 1 $\mu$Ci [$^3$H]-thymidine/well during the last 16 hours of exposure to the compounds. Cells were harvested with a cell harvester, using glass microfiber filters. The incorporation of [$^3$H]-thymidine was determined by retention of the acid insoluble fraction on filters and is expressed as CPM. The results of a representative experiment are shown in FIG. 3. FIG. 3A shows a titration curve using GC; FIG. 3B shows titration curves using GC and AB; and FIG. 3C shows similar titration curves for GC and GOMB; the GC concentration is indicated in the inset for panels B and C.

The results show that GOMB is 10-fold more potent than AB in inhibiting EBV-positive lymphoma cells, and importantly, that AB and GOMB interact synergistically with GC to inhibit proliferation of an EBV-associated tumor cell line.

EXAMPLE 5

Inducing Differentiation

Cancer cell differentiation was evaluated in a human leukemia cell line by nitroblue tetrazolium reduction (NBT) activity (Koeffler, Blood, 62: 709–721, 1983) or in a breast carcinoma cell line by lipid staining (Bacus et al., Mol. Carcinog. 3:350–362, 1990).

Figure 4:
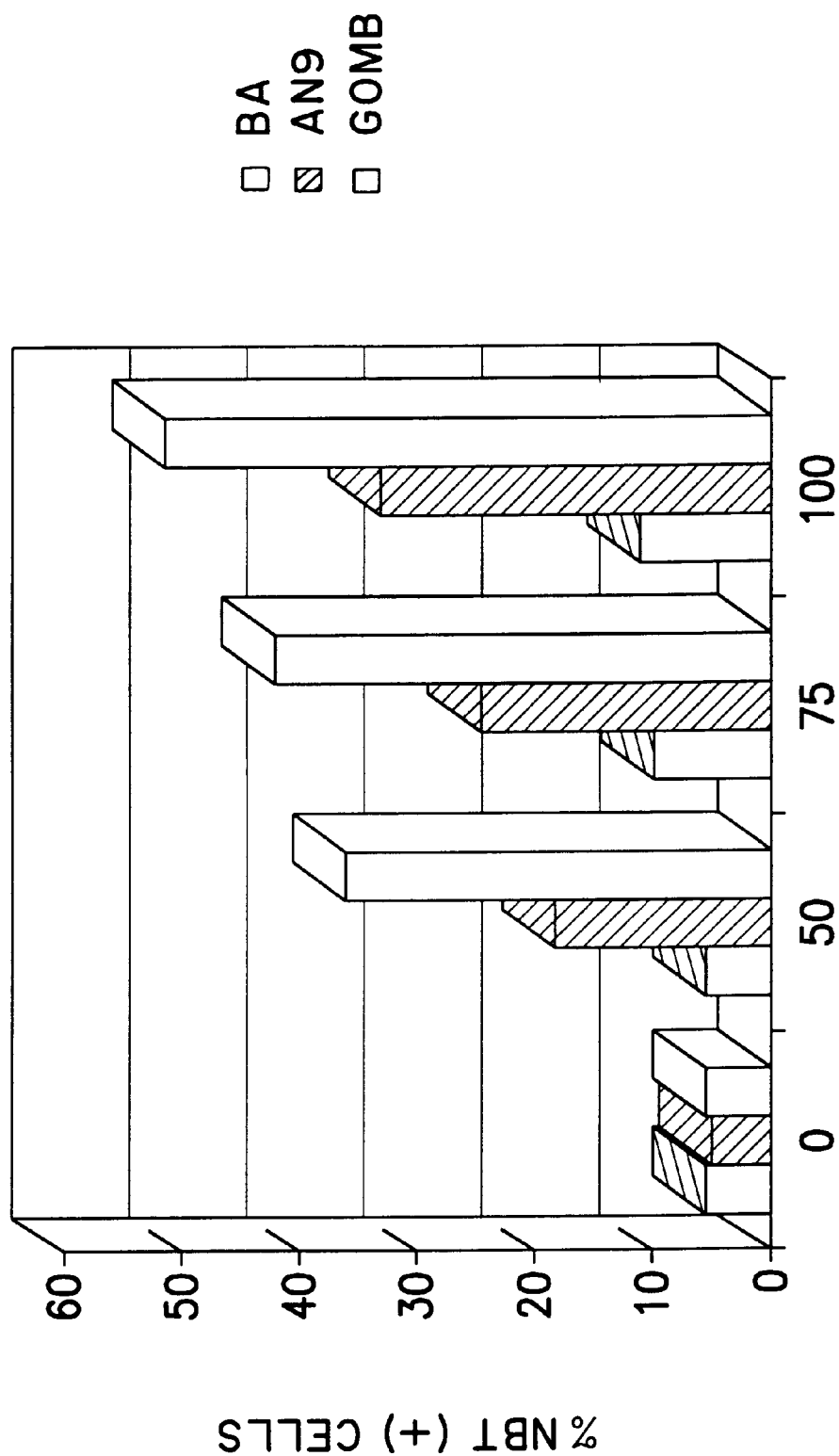
FIG. 4 is a bar graph showing the percentage of NBT-positive human leukemia cells for cells treated with AB, AN-9 and GOMB.

The differentiation ability of AB and GOMB with the human leukemia cell line HL-60 was compared to pivaloyoxylmethyl butyrate (AN-9). Briefly, HL-60 cells were incubated with the indicated concentration of AB, GOMB or AN-9 for three days, washed, resuspended in saline containing 0.1% NBT and stimulated with 0.4 $\mu$M phorbol ester for 30 minutes at 37° C. The cells were examined microscopically and at least 200 cells were scored. The results are provided graphically in FIG. 4 and demonstrate that GOMB is more active at inducing differentiation than either AB or AN-9.

In the case of the human breast carcinoma cell line Au565, 100%. Of the cells treated with 10 $\mu$M GOMB were positive for lipid staining whereas less than 1% of cells treated with the same concentration of AB were positive for lipid staining.

EXAMPLE 6

Inhibition of Cancer Cell Proliferation Assessed by the SRB Assay

Figure 5:
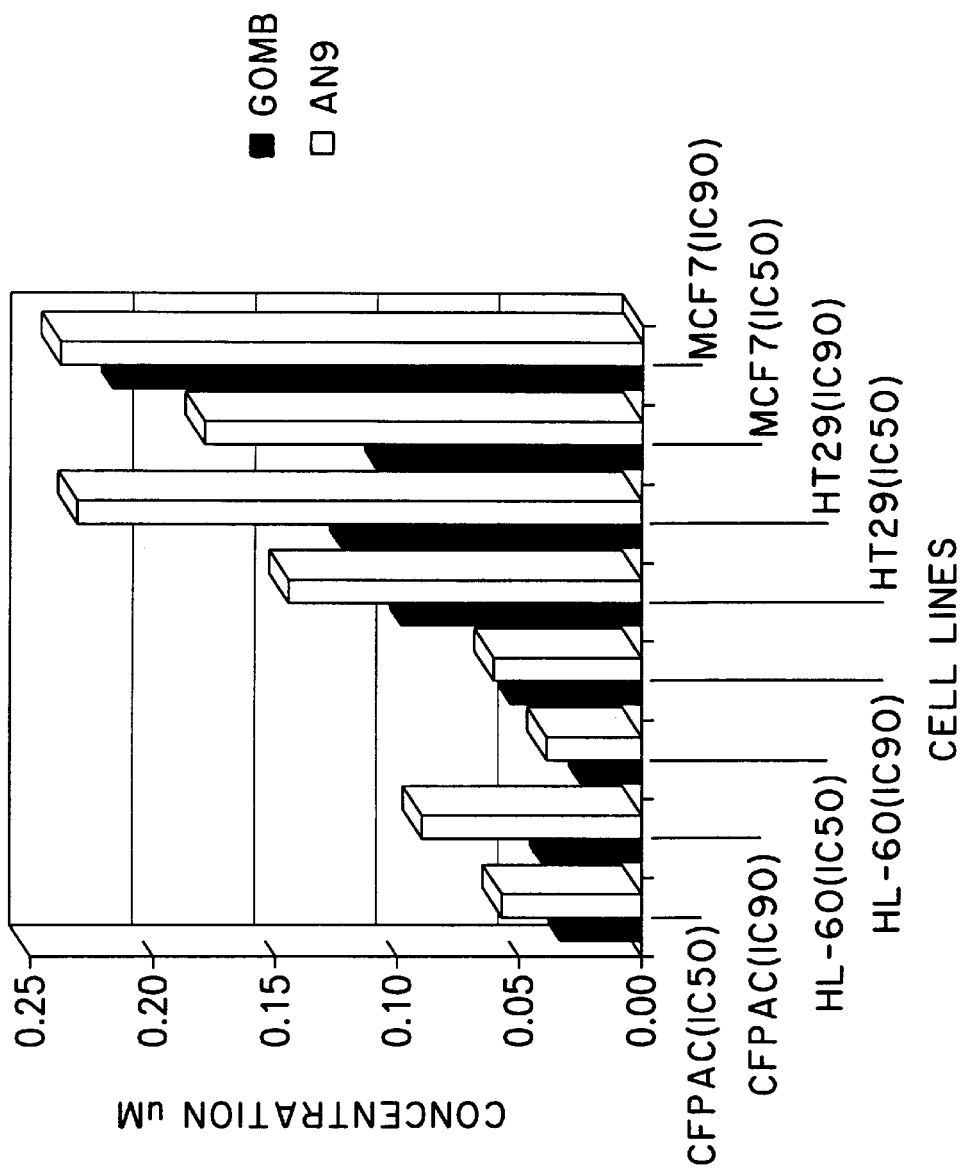
FIG. 5 is a bar graph comparing the IC50 and IC90 values of GOMB and AN-9 on the indicated cell lines treated in the SRB assay.

The inhibition of cell proliferation was measured in the indicated cancer cell lines using the sulforhoamine B (SRB) assay as described by Monks et al., J. Natl. Can. Inst. 83:757–766. The SRB assay is used to screen for anti-cancer drugs. A comparison of GOMB, AB and AN-9 demonstrates that GOMB exerts at least 100-fold greater activity than AB as measured by the $IC_{50}$ and $IC_{90}$ values (Table 4). GOMB also was 1.4- to 2.2-fold more active than AN-9 in 6 out of 8 of the $IC_{50}$ and $IC_{90}$ determinations. (Table 4 and FIG. 5).

TABLE 4

Comparison of AB, GOMB and AN-9 in the SRB Assay

| | CELL LINES | | | | | | | |
|---|---|---|---|---|---|---|---|---|
| | CFPAC | | HL-60 | | HT-29 | | MCF7 | |
| AGENT | $IC_{50}$ | $IC_{90}$ | $IC_{50}$ | $IC_{90}$ | $IC_{50}$ | $IC_{90}$ | $IC_{50}$ | $IC_{90}$ |
| AB | >4.0 | >4.0 | 1.644 | 3.455 | >4.0 | >4.0 | >4.0 | >4.0 |
| GOMB | 0.0325 | 0.0410 | 0.0245 | 0.0536 | 0.0982 | 0.123 | 0.109 | 0.218 |
| AN-9 | 0.0559 | 0.0898 | 0.0390 | 0.0599 | 0.144 | 0.231 | 0.180 | 0.238 |
| GOMB/AN9 | 1.72 | 2.2 | 1.6 | 1.11 | 1.4 | 1.9 | 1.65 | 1.01 |

EXAMPLE 7

Induction of Apoptosis

Apoptosis was measured as described by Telford et al., 1991, Cell Physiol. 24:447–459, in HL-60 cells and in the human erthroblastic cell line, K-562. Cells were treated with COMB for 3 days, fixed, stained with propidium iodine and analyzed by flow cytometrly for cell cycle distribution. A distinct subpopulation of cells was observed in a region below the G0-G1 cells. This region consisted of cells with fragmented DNA. The increase in apoptotic cells in HL-60 and K-562 cells lines treated with varying concentrations of COMB is shown in Table 5.

Induction of apoptosis by COMB and AB in MCF-7 cells was evaluated by staining cells with the WAF antibody and by Western blot analysis as described by Bacus et al., 1996, Oncogene 12:2535–2547. The percentage of cells expressing WAF was 13% in the controls and increased 623% in GOMB-treated cells. The results demonstrate that GOMB induces apoptosis in a dose-dependent manner and that COMB induces apoptosis at a 10-fold lower concentration than does AB(Table 6).

TABLE 5

Induction of Apaptosis in Human Leukemia Cells

| GOMB ($\mu$M) | % apoptotic cells HL-60 | % apoptotic cells K-562 |
|---|---|---|
| 5.0 | 9.4 | ND* |
| 12.5 | 14.9 | 9 |

TABLE 5-continued

Induction of Apaptosis in Human Leukemia Cells

| GOMB (µM) | % apoptotic cells HL-60 | % apoptotic cells K-562 |
|---|---|---|
| 25.0 | 15.8 | 18 |
| 37.5 | 36.3 | ND |

*ND, not determined.

TABLE 6

Apoptosis in Breast Cancer Cells

| Concentration | % Cells Expressing WAF | |
|---|---|---|
| (µM) | AB | GOMB |
| 10 | ND* | 36 |
| 25 | ND | 34 |
| 50 | ND | 79 |
| 100 | 23 | 81 |

*ND, not detected.

EXAMPLE 8

Induction of Hemoglobin Synthesis

Hb Measurement: HB was measured by benzidine staining of K562 cells after 5 days exposure to GOMB or AB according to the procedure of Fibach et al. (1989) [full cite]. Quantitative measurement of HbF in K562 culture or human erythroid cultures was determined by ion-exchange high pressure liquid chromatography (HPLC) as described by Fibach et al., Blood 81:1630–1635, 1993.

K562 cells: K562 is an erthroblast cell line that develops some properties of erythroid, megakaryocyte or monocyte cells, depending on the specific stimulus, when induced by different chemicals. K562 cells were grown in RPMI with 10% FCS, supplemented with 2 mM glutamine. Cells were incubated at 37° C. in a humidified, 5% $CO_2$ incubator.

Treatment of K562 cells with GOMB and AG showed that, on a molar basis, GOMB has a higher activity in inducing erythroid differentiation (hemoglobin accumulation) than does AB. This was evident from the higher proportion of Hb-containing cells per the total cell population (Table 7) as well as the total Hb content of the cultures (Tables 8). The extent of differentiation of the treated cultures was directly related to the drug dose. The diluents, DMF and water, had no effect on cell growth, cell viability or differentiation.

Erythroid cells: Erythroid cells were isolated from peripheral blood of healthy individuals by the method of Fibach (1993). The results showed that 0.2 mM GOMB increased HbF by 49.5% in cultured erythroid cells relative to untreated control cultures.

TABLE 7

Percentage K562 Cells Containing HbF

| Concentration (mM) | GOMB | AB |
|---|---|---|
| 0.01 | 6.3 ± 1.15 | ND |
| 0.05 | 12.3 ± 5.3 | 3 ± 2 |
| 0.10 | 29 | ND |

TABLE 8

HbF Synthesis in K562 Cells

| Concentration (mM) | GOMB | AB |
|---|---|---|
| 0.01 | 1.54* | 0.96 |
| 0.05 | 3.21 | 0.95 |
| 0.10 | 5.0 | 1.8 |
| 0.50 | — | 3.69 |

*HbF in µg/ml

We claim:
1. A compound represented by the formula:

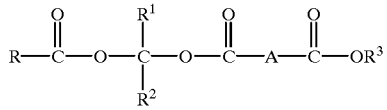

wherein
R is n-propyl, isopropyl, 1-methylpropyl, n-butyl, isobutyl, 1-methylbutyl, 2-methylbutyl, n-amyl, isoamyl, 1-, 2-, or 3-methylamyl, 2-ethylbutyl or benzyl, any of which can be optionally substituted with halo, trifluoromethyl, amino, alkoxy or aryl; or R is $C_3$ to $C_5$ linear alkenyl, optionally substituted with halo, trifluoromethyl, amino, alkoxy or aryl;

$R^1$ and $R^2$ are independently H, lower alkyl or lower alkenyl;

A is arylene or $C_1$ to $C_8$ alkylene, alkenylene or alkynylene, wherein alkylene, alkenylene and alkynylene are optionally substituted with one or more of hydroxy, halo, lower alkyl, alkoxy, carbonyl, thiol, lower alkylthio or aryl;

$R^3$ is H, lower alkyl, aryl, or —$CR^1R^2$—O—C(O)—R; or a pharmaceutically-acceptable salt thereof.

2. The compound of claim 1, wherein
R is n-propyl, 3-(phenyl)propyl, 2-propenyl or benzyl;
A is arylene or $C_1$ to $C_8$ alkylene, alkenylene or alkynylene, wherein alkylene, alkenylene and alkynylene are optionally substituted with one or more of hydroxy, halo, lower alkyl, alkoxy, carbonyl, thiol, lower alkylthio or aryl;
$R^3$ is H, lower alkyl, or —$CR^1R^2$—O—C(O)—R; or a pharmaceutically-acceptable salt thereof.

3. The compound of claim 1, wherein said compound is mono-(butyroyloxymethyl)glutarate, bis-(butyroyloxymethyl)glutarate, mono-(1-butyroyloxyethyl) glutarate, or bis-(1-butyroyloxyethyl)glutarate.

4. A pharmaceutical composition comprising a therapeutically-effective amount of a compound of any one of claims 1 to 3 and a pharmaceutically-effective carrier or diluent.

5. A pharmaceutical composition comprising a therapeutically-effective amount of a compound of any one of claims 1 to 3 with a therapeutically-effective amount of a pharmaceutical agent, wherein said agent is selected from the group consisting of a cytokine, an interleukin, an anticancer agent or anti-neoplastic agent, a chemotherapeutic agent, an antibody, a conjugated antibody, an immune stimulant, an antibiotic, a hormone antagonist or a growth stimulant.

6. The composition of claim 5 wherein said pharmaceutical agent comprises a cytotoxic agent.

7. The composition of claim 5 wherein said antibiotic is an antiviral nucleoside antibiotic selected from the group consisting of ganciclovir, acyclovir, and famciclovir.

8. The composition of claim 5 wherein said antibiotic is ganciclovir.

9. The composition of claim 5 wherein said chemotherapeutic agent is selected from the group consisting of alkylating agents, purine and pyrimidine analogs, vinca and vinca-like alkaloids, etopsides and etopside-like drugs, corticosteroids, nitrosoureas, antimetabolites, platinum based cytotoxic drugs, hormonal antagonists, anti-androgens and antiestrogens.

10. The composition of claim 5, wherein said cytokine is an interferon.

11. The composition of claim 5, wherein said immune stimulant is *Corynebacterium parvum* or a sarcolectin.

12. The composition of claim 5, wherein the chemotherapeutic agent is selected from the group consisting of tamoxifen, doxorubicin, 1-asparaginase, decarbazine, amacrine, procarbazine, hexamethylmelamine, mitosantrone and gemcitabine.

* * * * *